(12) United States Patent
Hwang et al.

(10) Patent No.: US 8,734,830 B2
(45) Date of Patent: May 27, 2014

(54) MANUFACTURING METHOD AND APPARATUS OF ULTRAFINE PARTICLES HAVING UNIFORM PARTICLE SIZE DISTRIBUTION

(75) Inventors: Sung Joo Hwang, Seoul (KR); Min Soo Kim, Jinju-si (KR); Jeong Soo Kim, Daejeon (KR); Kwang Ho Cha, Daejeon (KR); Won Kyung Cho, Jeonju-si (KR); Jun Sung Park, Daejeon (KR); Suk Jun Seo, Daegu (KR)

(73) Assignee: Korea United Pharm. Inc., Sejong-Si (KR)

( * ) Notice: Subject to any disclaimer, the term of this patent is extended or adjusted under 35 U.S.C. 154(b) by 252 days.

(21) Appl. No.: 13/054,423

(22) PCT Filed: Mar. 3, 2010

(86) PCT No.: PCT/KR2010/001318
§ 371 (c)(1),
(2), (4) Date: Apr. 5, 2011

(87) PCT Pub. No.: WO2010/150964
PCT Pub. Date: Dec. 29, 2010

(65) Prior Publication Data
US 2011/0200678 A1    Aug. 18, 2011

(30) Foreign Application Priority Data
Jun. 23, 2009 (KR) .................. 10-2009-0055743

(51) Int. Cl.
| | | |
|---|---|---|
| A61K 9/14 | (2006.01) |
| A61K 38/13 | (2006.01) |
| A61K 31/4196 | (2006.01) |
| A61P 19/00 | (2006.01) |
| A61K 31/41 | (2006.01) |
| A61K 31/56 | (2006.01) |
| A61K 31/4422 | (2006.01) |
| A61K 33/00 | (2006.01) |
| A61K 38/43 | (2006.01) |
| A61K 31/70 | (2006.01) |
| A61K 31/07 | (2006.01) |
| A61K 31/355 | (2006.01) |

(52) U.S. Cl.
USPC .................. 424/423; 424/489; 425/6

(58) Field of Classification Search
None
See application file for complete search history.

(56) References Cited

U.S. PATENT DOCUMENTS 5,192,528 A * 3/1993 Radhakrishnan et al. ...... 424/45
5,770,559 A   6/1998 Manning et al.
(Continued)

FOREIGN PATENT DOCUMENTS

JP    11-514367 A    12/1999
JP    2003-501245 A    1/2003
(Continued)

OTHER PUBLICATIONS

Colloids [online] retrieved on Sep. 4, 2013 from: http://chemwiki.ucdavis.edu/Physical_Chemistry/Physical_Properties_of_Matter/Solutions/Colloid; 4 pages.*
Office Action issued in Japanese Patent Application No. 2011-52003 on May 8, 2012 along with English translation, 8 pages.

*Primary Examiner* — Ernst Arnold
(74) *Attorney, Agent, or Firm* — Rothwell, Figg, Ernst & Manbeck, P.C.

(57) ABSTRACT

The present invention relates to a novel technology for forming fine particles with a size of 0.0~23 microns from a solid that can be dissolved in a liquid solvent and is not decomposed by heat. The particle preparation technology according to the present invention may be applicable to the fields of food, cosmetics, biopolymer, polymer compositions, and pharmaceuticals.

11 Claims, 5 Drawing Sheets

(56) References Cited

U.S. PATENT DOCUMENTS

| | | | |
|---|---|---|---|
| 5,851,453 A | 12/1998 | Hanna et al. | |
| 6,056,791 A | 5/2000 | Weidner et al. | |
| 7,279,181 B2 | 10/2007 | Chattopadhyay et al. | |
| 2004/0026319 A1 | 2/2004 | Chattopadhyay et al. | |
| 2005/0142206 A1* | 6/2005 | Brown et al. | 424/490 |
| 2006/0062848 A1* | 3/2006 | German et al. | 424/464 |
| 2007/0116729 A1* | 5/2007 | Palepu | 424/400 |
| 2010/0167051 A1* | 7/2010 | Goia et al. | 428/402 |

FOREIGN PATENT DOCUMENTS

| | | |
|---|---|---|
| JP | 2004-045098 A | 2/2004 |
| JP | 2004-105953 A | 4/2004 |
| WO | 97/14407 A1 | 4/1997 |
| WO | 00/75281 A2 | 12/2000 |
| WO | 2007/136830 A2 | 11/2007 |

* cited by examiner

MANUFACTURING METHOD AND APPARATUS OF ULTRAFINE PARTICLES HAVING UNIFORM PARTICLE SIZE DISTRIBUTION

CROSS REFERENCE TO RELATED APPLICATIONS

This application is a 35 U.S.C. §371 National Phase Entry Application from PCT/KR2010/001318, filed Mar. 3, 2010, and designating the United States, which claims priority under 35 U.S.C. §119 to Korean Patent Application No. 10-2009-0055743 filed Jun. 23, 2009, which is incorporated herein in its entirety.

FIELD OF THE INVENTION

The present invention relates to a method and apparatus for preparing fine particles having uniform particle size distribution with an average particle size of 0.0~23 micron, from solids soluble in a liquid solvent, in which 10% or less of prepared powder has a size of less than 0.02 micron while 90% or more has a size of less than 3 micron.

DESCRIPTION OF THE PRIOR ART

Many drugs, which are currently used as medicines or being researched, have sparing-solubility in an aqueous solvent. Thus, while being absorbed into a body by administration, they show a low solubility and a low elution rate in the digestive juice, thereby causing a problem of low bioavailability. Accordingly, some technologies to solve the problem have been used, in which the elution rate of a drug is increased by reducing a particle size and maximizing a particle surface area, and thereby bioavailability of a drug having an elution rate of a rate-limiting step is increased. Methods for preparing fine particles include a Bottom-Up approach using precipitation, and a Top-Down approach using milling.

One of methods using precipitation is disclosed in GB 2269536. In the method disclosed in this patent, a solution of a sparingly water-soluble activator and a water-miscible organic solvent is mixed with a relatively large amount of water, under the condition where a water-insoluble colloid exists in an organic solvent or a water-soluble colloid exists in water, so as to stabilize a to-be-formed hydrosol of the activator. Then, the hydrosol having solid activator particles is prepared and is dried into a form capable of being re-suspended in water as required.

Also, another method using precipitation is disclosed in D 19,637,517 and U.S. Pat. No. 7,105,176. In the method disclosed in this patent, a drug suspension is placed in a solution state by adding another solvent or changing a process condition (temperature or pressure), the resultant solution is dissolved or dispersed in a proteinaceous protective colloidal aqueous molecular dispersant or a colloidal dispersant, a protective colloid is aggregated together with an active compound from the dispersed material, and then the solvent is removed.

The methods according to the above mentioned patents are inefficient because they require a stabilizer for inhibiting crystal growth, and an additional process/time for removing water and a solvent. Besides the above mentioned patents using precipitation, there is a supercritical fluid process.

For the past 15 years, various techniques and devices for preparing powder by using a compressed fluid or a supercritical fluid have been suggested, and most of the techniques use carbon dioxide in the process.

Various techniques and patents which have been introduced to date are divided into three sections: rapid expansion of supercritical solutions (RESS), supercritical antisolvent precipitation (SAS), and particles generation from gas saturated solutions (PGSS).

First, RESS is a technology where a solid is dissolved in a supercritical solvent to prepare a supercritical solution, and the supercritical solution is expanded to atmospheric pressure so as to induce precipitation of the dissolved solid. Based on the principle of such RESS, variously modified technologies were disclosed in DE 2943267, U.S. Pat. No. 4,582,831, U.S. Pat. No. 4,734,451, and U.S. Pat. No. 4,970,093.

The most serious defect of the RESS is that most solids have low solubility in a supercritical solvent. Also, it is very difficult to adjust the particle size and morphology of generated powder.

SAS (supercritical antisolvent precipitation) indicates a technology based on the precipitation from a solid solution induced by a supercritical antisolvent (aka ASES, SEDS, GAS, SAS, or the like). This technology is described in detail in "Supercritical antisolvent precipitation of micro and nano particles, Recerchon, 1999, J. Supercrit. Fluids, 15, 1-21". In preparing particles by this technology, a liquid solvent used for preparing a solid solution has to be completely dissolved in a supercritical antisolvent while a solid must not be dissolved in the supercritical antisolvent at all. Unfortunately, many solid particle preparation methods using the SAS have many problems. However, when a particle preparation method by using SAS is successfully applied, it is possible to adjust the particle size (from 1 micron hundreds micron) and the morphology of powder to a considerable extent. Also, for the SAS, various application examples and modified technologies were suggested. For example, Hanna and York (U.S. Pat. No. 5,851,453) suggested a particle preparation technology using a coaxial injector for performing both the mixing and spraying of a supercritical antisolvent and a solid solution in the SAS process (a process by this technology makes it possible to form particles by using a mechanical discharge power by the flow velocity of two fluids at the outflow part at the end of the injector).

Also, there have been suggested various technologies for optimizing the SAS particle preparation method by varying process applications, using other fluids (e.g. in U.S. Pat. No. 6,063,138, organic solvent-supercritical antisolvent, supercritical solvent-supercritical antisolvent, and liquid solvent-organic solvent-supercritical antisolvent), and modifying an apparatus for preparing particles.

Lastly, PGSS (particles generation from gas saturated solutions) was suggested by Weidner and Knez (EP744992, WO9521688), and indicates a process for preparing particles by dissolving supercritical carbon dioxide in a molten polymer in a heated container, and spraying the resultant mixture to a container at low pressure. The supercritical carbon dioxide is dissolved in various polymers, thereby liquefying the polymer (due to the drop of glass transition temperature of the polymer). The polymer solution formed by dissolving the supercritical carbon dioxide in the polymer is rapidly expanded in the low-pressure container, thereby forming polymer droplets. The formed polymer droplets are cooled by the expansion of carbon dioxide (Joule-Thomson effect), thereby forming powder. From researches on a PGSS particle preparation method, the smallest particle ever reported has an average size of 7.8 micron.

As other processes for forming fine droplets of dyes so as to increase the coating efficiency (which are related to a different object of the present invention), there have been suggested various spray coating processes based on the principle of PGSS particle preparation, disclosed in U.S. Pat. No. 5,057,342, U.S. Pat. No. 5,066,522, U.S. Pat. No. 5,009,367, U.S. Pat. No. 5,106,650, U.S. Pat. No. 5,211,342, U.S. Pat. No. 5,374,305, and U.S. Pat. No. 5,466,490. In such processes, a supercritical fluid was used to decrease the viscosity of a solution to be sprayed. Also, the patents are characterized in that they are effective in removing and reducing a volatile organic matter, and some of them suggest a powder preparation technology by spray.

EP 677332, U.S. Pat. No. 5,639,441, U.S. Pat. No. 6,095,134, and U.S. Pat. No. 6,830,714 disclose particle preparation processes by the modified-PGSS. Especially, Carbon dioxide Assisted Nebeulization with a Bubble Dryer (CAN-BD), suggested by Sievers, is the most representative in various modified-PGSS processes. Such processes are characterized in that an aqueous solution or an organic solution including a to-be-particalized solid dissolved therein comes in contact with the flow of carbon dioxide by using a T-shape or Y-shape union with a very small internal volume (less than 1 µl). Then, the resultant unblended mixture (referred to as suspension, emulsion, micelle dispersion, etc.) of liquid and supercritical fluid is sprayed as very small droplets through a long capillary nozzle with a thin inside diameter (125 micron), and the sprayed droplets are dried to provide particles. Various researches on a particle preparation method by using this technology have been reported by many researchers.

In CAN-BD suggested by Sievers, et al., there is a possibility that carbon dioxide may not be sufficiently dissolved in a liquid solution due to the very short contact time of the liquid solution with carbon dioxide, thereby making it difficult to adjust the morphology and particle size of prepared particles. In order to complement such a defect, Reverchon suggested, in WO 03004142, a Supercritical Assisted Atomization (SAA) process which introduces a saturator in a particle preparation process, the saturator being designed for completely mixing a solid-dissolved aqueous or organic solution with supercritical carbon dioxide.

The SAA is characterized in that the saturator is introduced, instead of the T-shape or Y-shape union with a very small internal volume, so as to completely blend a liquid solution with supercritical carbon dioxide. The resultant mixed liquid of the liquid solution and supercritical carbon dioxide, formed through the saturator, is sprayed onto a high-temperature heated (150° C.) nitrogen-flow through a capillary nozzle, so as to form fine droplets. Then, the formed fine droplets are dried to provide fine particles (0.02~10 micron).

However, the SAA process requires a highly complicated preparation apparatus because it uses high-temperature heated nitrogen for drying fine droplets, and has a defect in that the yield of fine particles prepared from a small-scale experiment (about 1 g) in a laboratory is very low (about 50%). Also, since only supercritical carbon dioxide is used as a spray propellant, prepared powder may have wide particle-size distribution.

The inventor of the present invention succeeded in preparing fine particles having a uniform particle size, and increased solubility, elution, and bioavailability by applying the above described supercritical fluid processes to sparingly soluble various drugs, and disclosed technologies for this in KR 0529757, KR 0592511, KR 0667366, KR 0667367, KR 0673810, and KR 0742571. However, such a supercritical fluid technology, despite its many advantages, has a problem in that it is difficult to apply its process with an established validation to mass production. Thus, the technology has not yet been applied to manufacture of products.

A technology for preparing fine particles, which uses wet milling by a top-Down approach, is disclosed in U.S. Pat. No. 5,145,684. In the method according to the patent, a prepared pharmaceutical material is added to a liquid medium in which the pharmaceutical material is hardly dissolved, a surface modifying agent is added to prepare a premix, and then the average particle size of the premix in the dispersed material is reduced to less than 400 nm by using a mechanical means, such as a ball mill, an attritor mill, a vibration mill, a sand mill, and a bead mill. The dispersed material exists as a suspension, and thus is subjected to a drying process to obtain solid fine particles. The method according to the above mentioned patent requires a long time for a milling process, and may be polluted by a milling medium. Moreover, the method requires an additional inefficient process to remove water that is mainly used as a liquid dispersion medium, and is difficult to be applied in a medicine that can be chemically damaged by water. Also, the method has a disadvantage in that the particle size of the raw material for the method is required to be previously adjusted to some extent.

One technology for preparing fine particles, which uses a high pressure homogenizer by a top-Down approach, is disclosed in U.S. Pat. No. 5,858,410. In the technology according to the patent, an active material which is hardly dissolved or is slightly dissolved in water, aqueous media or organic solvents, is added with a surfactant and a stabilizer, and is subjected to a high-pressure/homogenizing process by a piston-gap homogenizer so as to prepare a nanosuspension. Also, there are other technologies for preparing fine particles, disclosed in PCT/EP00/06535 and U.S. Pat. No. 6,884,436. In the technology disclosed in PCT/EP00/06535, an active substance and a stabilizer are dispersed by using, as a dispersion medium, a non-aqueous liquid (liquid polyethylene glycol, or anhydrous glycerin) with a lower vapor pressure, instead of water, and then are homogenized at lower temperature by using a piston-gap homogenizer, a jet-stream homogenizer, an ultrasonic homogenizer, or the like. In the technology disclosed in U.S. Pat. No. 6,884,436, an active substance is dissolved in a water-miscible organic solvent and mixed with water (as a nonsolvent), and then is precipitated to generate the preliminary suspension, and the suspension is subjected to high-shear mixing or heat energy to provide fine particles. However, the technologies using the high-pressure homogenizer, according to the above described patents, include processes requiring high energy, and have to use a raw material whose particle size has been adjusted in a micro-size prior to the processes. Also, the technologies may have problems: chemical damage due to many processes and the generation of heat energy during the processes; and metal contamination generated by the wear of an apparatus due to a strong shear stress. Also, there exists a possibility that the active substance may be hydrolyzed because water is frequently used as the dispersion medium.

Besides the above described technologies, there is a spray-drying process (U.S. Pat. No. 5,624,530, and US 2004/0175328A1), that is, one of Bottom-Up methods, in which a drug solution is dried by being sprayed in hot wind, and entrained in the form of fine drops in air stream. This process can be used in relatively low temperatures where a used solvent can be volatilized in a short time, and does not have a significant influence on the stability of a drug due to the drug's very short exposure time, even under a high temperature condition. Also, this process may be used as a single process which does not require an additional particle size uniformization or an additional drying process, or may be used as a continuous process capable of being automated and monitored so that it can be easily scaled up in accordance with GMP. However, in most cases, micro-size particles, instead of nano particles, are obtained, and also there is a problem in a yield. It can be said that this is a limitation of the spray-drying process, compared to a supercritical fluid process in which nano particles with a uniform particle size can be prepared.

Accordingly, in order to complement the disadvantages of the above described various fine-particle preparation technologies, a novel particle preparation method has been made. In the novel method according to the present invention, a mixture of a liquid solution and a compressed fluid is injected together with heated compressed gas, thereby facilitating the movement of materials during the formation of particles. Thus, it is possible to form particles having a more fine size (20~3000 nm) compared to a conventional particle preparation process. In addition, in the method, the process of removing a solvent is very effective because it is performed as a single process, and it is possible to prepare powder with narrower and more uniform particle size distribution than a conventional method.

In a novel particle preparation process suggested according to the present invention, a mixture of a liquid solution and a compressed fluid is sprayed together with heated compressed gas, thereby facilitating material transfer during particle formation. Thus, it is possible to form particles with a more fine particle size (20~3000 nm) than a conventional particle preparation process, and to prepare powder with more fine and more uniform particle size distribution than a conventional process. Moreover, the method of the present invention has an advantage in that it can be applied to the preparation of nano particles of water-soluble drugs or protein drugs while in a wet-grinding method, the drugs cannot be prepared into nano particles.

Also, the method of the present invention can use most organic solvents and water as well as volatile organic solvents with a boiling point of less than 120° C., unlike conventional processes, and is more advantageous in that the particle size of a raw material is not required to be considered, compared to a conventional wet-grinding method requiring an additional process for adjusting the particle size of a raw material.

SUMMARY OF THE INVENTION

Accordingly, through researches on a method for preparing ultra-fine particles having uniform particle size distribution, the inventors of the present invention found that when a mixture of a liquid solution including a to-be-particlized solid and a compressed fluid is sprayed together with heated compressed gas, it is possible to prepare ultra-fine particles with highly uniform particle size distribution.

Accordingly, the present invention provides a novel method and apparatus for preparing ultra-fine particles having uniform particle size distribution.

In order to achieve the object, the present invention provides a novel and efficient method for preparing fine particles from a compressed fluid, the fine particles having sizes of tens of nanometers to several micros.

In the process according to the present invention, since the mixture of a liquid solution and a compressed fluid is sprayed together with heated compressed gas, it is possible to prepare fine particles having an average size of 0.02~3 micron with highly dense and uniform particle size distribution (which cannot be achieved by conventional other particle preparation methods using supercritical fluids).

The particle preparation method according to the present invention can replace the following processes by varying the kinds of the solvent and solid.

1) conventional various methods for preparing solid fine particles by using water and organic solvent 2) methods for preparing a solid fine particle composition in the form of a capsule or matrix including two or more materials, by using water and organic solvent The novel method of preparing ultra-fine particles by using a supercritical fluid, according to the present invention, includes the steps of:

1) preparing a liquid solution by dissolving a solid solute in a liquid solvent, and injecting the prepared liquid solution onto the flow of compressed fluid, thereby contacting the two materials with each other;

2) completely blending the two fluids by injecting them into a mixing unit; and 3) spraying the formed mixed fluid, together with heated compressed gas, onto the flow of drying gas via a nozzle, thereby forming fine droplets, and then forming fine particles by drying the droplets.

Also, the present invention provides an apparatus for preparing ultra-fine particles with uniform particle size distribution, the apparatus including:

a device for preparing and transferring a liquid solution (or dispersion) of a solute;

a compressed-fluid storing vessel/transfer device for storing a supercritical compressed fluid;

a mix-reactor for continuously contacting the liquid solution (or dispersion) of the solute with the supercritical compressed fluid to form a single-phase or colloidal mixture fluid;

a compressed/drying gas supplying device for carrying heated compressed/drying gas;

a reactor for spray-drying the single-phase or colloidal mixture fluid from the mix-reactor and the heated compressed/drying gas into an atmospheric pressure evaporation chamber through inside and outside of a coaxial nozzle, respectively, to form ultra-fine particles; and a collecting device for collecting the formed ultra-fine particles.

In the present invention, the compressed fluid may be at least one mixture selected from the group including fluorinated hydrocarbons including chlorofluorocarbons, hydrochlorofluorocarbons, hydrofluorocarbons, and fluorocarbons, [e.g. R-10(tetrachloromethane), R-11 (trichlorofluoromethane), R-12(dichlorofluoromethane), R-13(chlorotrifluoromethane), R-14, R-20, R-21, R-22(chlorodifluoromethane), R-23, R-30(dichloromethane), R-40, R-41, R-111, R-112, R-113, R-114, R-115, R-116(hexafluoroethane), R-122, R-123, R-124, R-125, R-130, R-131, R-132, R-133, R-134, R-140, R-141, R-142, R-143, R-150, R-151, R-152, R-160(chloroethane), R-161, R-211, R-212, R-213, R-214, R-222, R-224(trichlorotetrafluoropropane), R-235 (chloropentafluoropropane), or the like], dimethylether, diethylether, diisopropylether, di-tert-butylether, carbon dioxide and ammonia, with a temperature range of 30 to 90° C. and a pressure range of 60 to 300 bar, preferably with a temperature range of 40 to 80° C. and a pressure range of 75 to 120 bar. Preferably the compressed fluid may be at least one mixture selected from the group including fluorinated hydrocarbons, ethers, and carbon dioxide, and more preferably, may be carbon dioxide.

In the present invention, the liquid solvent may be at least one mixture selected from the group including purified water, alcohols (methanol, ethanol, propanol, isopropanol, butanol, and octanol), ketones (acetone, methylethylketone, and methylisobutylketone), N-hexane, ethylacetate, dichloromethane, chloroform, acetic acid, N-methylpyrrolidone, dimethyl sulfoxide, dimethylamide, and dimethylformamide.

In the present invention, the nozzle indicates a device capable of spraying a single-phase or colloidal mixture including a compressed fluid and a liquid solution, together with heated compressed gas, at a spray outflow part, which allows the mixture to contact with the heated compressed gas. Also, the nozzle employs a multiple-fluid nozzle for two or more fluids, such as a multiple-fluid coaxial nozzle.

The coaxial nozzle includes cylindrical tubes, which have different inside diameters, and are disposed on the common central axis. Also, the nozzle has a conic end portion for efficiently performing mixing and spraying of fluids flowing out through respective flow channels.

A physiological active substance, which may be used as a solid solute in the present invention, may include, but not limited to, at least one mixture selected from the group including compounds having physiological activity, such as penicillin-based antibiotics, tuberculosis therapeutic agents, leprosy therapeutic agents, anti-anaerobe & antiprotozoal agents, antifungal agents, antivirals, antimalarial agents, anthelmintics, cephalosporin-based antibiotics, other beta-lactam-based antibiotics, aminoglycoside-based antibiotics, macrolide-based antibiotics, quinolone-based antibiotics, tetracycline-based antibiotics, sulfa drugs, external antimicrobial agents, stomatitis therapeutic agents, oral disinfectants, vaginal infection therapeutic agents, antitumor agents, anticancer agents, hematopoietics, anticoagulants, antithrombotic agents, platelet aggregation-inhibiting agents, thrombolytic agents, hemostatic agents, blood coagulation agents, circulation-improving agents, hemorrhoid drugs & varix therapeutic agents, heart failure therapeutic agents, other antihypertensives, antihyperlipidemic agents, antimigraine, antihypotensives, other cardiovascular system drugs, antiarrhythmic agents, α blocking agents, β blocking agents, diuretics, vasodilators, calcium channel antagonists, ACE inhibitors, nonspecific α, β blocking agents, vaccines, immunoglobulins, other biological agents, antacids & adsorbents, other medicines for stomach, appetite suppressants, anti-ulcerative drugs, H2 blocking agents, proton pump inhibitors, other anti-ulceratives, digestants, gastrointestinal motility regulators and anticonvulsants, medicines for intestinal disorders, purgatives, laxatives, antiemetic drugs, bile acid secretion promoters & liver protective drugs, female hormone drugs, bone metabolism drugs, oral contraceptives, androgen, anabolic steroids, adrenocortical hormones, insulin drugs, oral hypoglycemic agents, gonadotropin hormone, thyroid hormone and drugs, antithyroid drugs, antihistamine & antiallergic drugs, immunosuppressive drugs, immunostimulants, general anesthetics, antimanic drugs, central nervous system active agents, Antiparkinsonian, psychotropic, dizziness therapeutic agents, arthritis therapeutic agents & antirheumatoid agents, muscle relaxants, anti-inflammatory enzymes, antigout drugs, other neuromuscular drugs, local anesthetics, drugs for neuromuscular disorders, narcotic analgesics, nonsteroidal antiinflammatory/analgesic agents, COX-2 specific NSAIDs, anticonvulsants, sedative-hypnotic drugs and neuroleptics, antipsychotic agents, major tranquilizers, antidepressants, respiration accelerating agents, bronchodilators, bronchial asthma drugs, antitussive expectorant agents, rhinitis drugs, leukotriene regulatory agents, mydriatic agents, miotic agents, glaucoma therapeutic agents, cataract therapeutic agents, artificial tears, cornea softening/protective agents, other ophthalmics, genitourinary system smooth muscle relaxants, uterine stimulant pitocin, vaginal condition related agents, prostatitis/prostatic hypertrophy related agents, impotence therapeutic agents, and other pharmaceutical substances/preparations.

Representative examples of the physiological active substance, according to a general pharmaceutical use, are as follows.

Penicillins: Amoxicillin, Piperacillin sodium, Sultamicillin tosylate

Cephalosporins; First Generation: Cefadroxil, Cefadroxil Monohydrate, Cefatrizine, Cefazedone sodium, Cefazolin Sodium, Ceftezole Sodium, Cephalexin, Cephradine Cephalosporins; Second Generation: Cefaclor, Cefamandole Nafate, Cefmetazole Sodium, Cefminox Sodium, Ceforanide, Cefotetan Disodium, Cefotiam, Cefotiam HCl, Cefoxitin Sodium, Cefprozil, Cefuroxime axetil, Cefuroxime sodium Cephalosporins; Third Generation: Cefdinir, Cefdinir Monohydrate, Cefdinir Hemihydrate, Cefditoren Pivoxil, Cefixime, Cefmenoxime, Cefoperazone Sodium, Cefotaxime Sodium, Cefpiramide Sodium, Cefpodoxime Proxetil, Ceftazidime, Cefteram Pivoxil, Ceftizoxime Sodium, Ceftriaxone Sodium Cephalosporins; Fourth Generation: Cefepime HCl, Cefpirome sulfate Miscellaneous Beta-Lactams: Aztreonam, Carumonamsodium, Ertapenemsodium, Meropenem Aminoglycosides: Amikacin Sulfate, Gentamicin Sulfate, Isepamicin Sulfate, Micronomicin Sulfate, Netilmicin Sulfate, Ribostamycin Sulfate, Kanamycin Sulfate, Tobramycin, Tobramycin Sulfate, Vancomycin HCl Macrolides: Azithromycin, Clarithromycin, Erythromycin, Erythromycin propionate, Midecamycinacetate, Roxithromycin, Spiramycin, Telithromycin Quinolones: Ciprofloxacin HCl, Enoxacin, Gatifloxacin, Gemifloxacin methansulfonate, Levofloxacin, Lomefloxacin HCl, MoxifloxacinHCl, Norfloxacin, Ofloxacin, Pefloxacin methanesulfonate, Pipemidic Acid, Pipemidic acid trihydrate, Tosufloxacin tosylate Tetracyclines: Doxycycline guaiacolsulfonate, Doxycycline hyclate, Doxycycline monohydrate, Methacycline, Minocycline HCl, Oxytetracycline HCl, Tetracycline HCl Miscellaneous antibiotics: Chloramphenicol, Clindamycin HCl, Linezolid, Rifaximin, Sodium fusidate, Teicoplanin, Thiamphenicol, Tigecycline Antibiotics: Skin & Mucous Membrane: Bacitracin, Chlorhexidine Gluconate, Fusidic Acid, Mupirocin, Mupirocin Calcium, Neomycin Sulfate, Nitrofurazone, Silver Sulfadiazine Vaginal anti-infective agents: Isoconazole Nitrate, Sertaconazole nitrate, Ciclopirox Olamine, Clotrimazole Antitubercular Agents and Antileprotics: Cycloserine, Enviomycin Sulfate, Ethambutol HCl, Isoniazid, Prothionamide, Pyrazinamide, Rifampicin, Dapsone Anti-Anaerobe & Antiprotozoal Agents, Antifungal Agents, Anthelmintics, Antimalarial Agents: Chloroquine Phosphate, Metronidazole, Ornidazole, Tinidazole, Amphotericin B, Butenafine HCl, Fluconazole, Griseofulvin, Itraconazole, Ketoconazole, Micafungin sodium, Nystatin, Terbinafine HCl, Albendazole, Flubendazole, Mebendazole, Praziquantel, Hydroxychloroquine Sulfate, Primaquine Phosphate Antiviral Agents: Acyclovir, Didanosine, Efavirenz, Emtricitabine, Enfuvirtide, Entecavir, Famciclovir, Indinavir sulfate, Inosiplex, Interferon Beta-1a, Interferon Beta-1b, Lamivudine, Lopinavir, Nevirapine, Oseltamivir phosphate, Peginterferon Alpha-2a, Peginterferon Alpha-2b, Raltegravir potassium, Ribavirin, Ritonavir, Telbivudine, Tenofovir disoproxyl fumarate, Valacyclovir HCl, Valganciclovir hydrochloride, Zalcitabine, Zanamivir, Zidovudine Hepatopoietic agents: Oprelvekin, Erythropoietin alfa, Darbepoetin alpha Anticoagulants, antithrombotic agents, platelet aggregation-inhibiting agents, thrombolytic agents: Fondaparinux sodium, Nadroparin, Nafamostat mesilate, Sarpogrelate HCl, Tirofiban hydrochloride monohydrate, Abciximab, Argatroban, Aspirin, Cilostazol, Clopidogrel, Clopidogrel besylate, Clopidogrel bisulfate, Clopidogrel camsylate, Clopidogrel napadisilate monohydrate, Clopidogrel resinate, Dipyridamole, Ticlopidine HCl, Trapidil, Triflusal, Streptokinase, Urokinase, Limaprost, Tenecteplase Hemostatics, Coagulants: Adrenochrome Monoaminoguanidine Methanesulfonate, Aminocaproic Acid, Carbazochrome sodium sulfonate, P-aminomethyl benzoic acid, Tranexamic Acid, Vitamin K1

Circulatory Improvement Agents: Buflomedil HCl, Buflomedil pyridoxal phosphate, Citicoline, Ergoloid mesylate, Gamma-oryzanol, Ibudilast, Kallidinogenase, Nicametate Citrate, Pentoxifylline, Vinpocetine, Viquidil HCl Hemorrhoidal, Phlebitis & Varicose Preparations: Diosmin, Dobesilate calcium Antitumor agents, Antineoplastics: Aclarubicin HCl, Aldesleukin(rhIL-2), Alemtuzumab, Altretamine, Amifostine, Amsacrine, Anagrelide HCl, Anastrozole, Azacitidine, BCG Connaught Strain, BCG Strain Tice, Belotecan, Bevacizumab, Bicalutamide, Bleomycin HCl, Bortezomib, Buserelin Acetate, Busulfan, Capecitabine, Carboplatin, Carmofur, Carmustine, Cetuximab, Chlorambucil, Cinoxacin, Cisplatin, Cladribine, Cyclophosphamide, Cyproterone Acetate, Cytarabine, Dacarbazine, Dactinomycin, Dasatinib, Daunorubicin HCl, Decitabine, Docetaxel, Doxifluridine, Doxorubicin HCl, Enocitabine, Epirubicin HCl, Erlotinib HCl, Estramustine sodium phosphate, Etoposide, Exemestane, Floxuridine HCl, Fludarabine phosphate, Fluorouracil, Flutamide, Formestane, Gefitinib, Gemcitabine HCl, Gemtuxumab ozogamicin, Goserelin Acetate, Heptaplatin, Hydroxyurea, Ibritumomab tiuxetan, Idarubicin HCl, Ifosfamide, Imatinib mesylate, Interferon Alpha, Interferon Alpha-2a, Interferon Alpha-2b, Interferon Gamma, Irinotecan HCl, Lapatinib ditosylate, L-asparaginase, Lentinan, Letrozole, Leuprorelin acetate, Levamisole HCl, Lomustine, Megestrol Acetate, Melphalan, Mercaptopurine, Methotrexate, Mitomycin C, Mitotane, Mitoxantrone HCl, Nimustine HCl, Oxaliplatin, Paclitaxel, Pemetrexed disodium heptahydrate, Pentamidine Isethionate, Pirarubicin HCl, Polysaccharide K, Procarbazine HCl, Raltitrexed, Rituximab, Sizofuran, Sodium iodide, Sorafenib tosylate, Sunitinib, Sunitinib malate, Tamoxifen Citrate, Tegafur, Temozolomide, Thalidomide, Thioguanine, Topotecan HCl, Toremifene citrate, Trastuzumab, Trimetrexate, Triptorelin acetate, Triptorelin pamoate, Ubenimex, Vinblastin sulfate, Vinorelbine, *Viscum album*

Heart Failure: Denopamine, Digoxin, Ubidecarenone

Other Antihypertensives: Aliskiren hemifumarate, Bosentan hydrate, Clonidine, Clonidine HCl, Methyldopa, Temocapril hydrochloride Antilipemic Agents: Atorvastatin calcium, Cerivastatin sodium, Ciprofibrate, Etofibrate, Ezetimibe, Fenofibrate, Fluvastatin Sodium, Lovastatin, Nicotinic acid, Pitavastatin calcium, Pravastatin Sodium, Probucol, Rosuvastatin calcium, Simvastatin Migraine Drugs: Almotriptan maleate, Ergotamine tartrate, Flunarizine HCl, Rizatriptan benzoate, Sumatriptan, Sumatriptan Succinate Hypotension Drugs Dopamine HCl, Midodrine HCl Miscellaneous Cardiovascular System drugs: Ifenprodil Tartrate, L-carnitine, Nicametate Citrate, Nicorandil, omega-3-acid ethyl esters90, Raubasine, Trimetazidine HCl Antiarrhythmic Agents: Amiodarone HCl, Flecamide Acetate, Mexiletine HCl, Procainamide HCl, Sotalol HCl Alpha Blockers: Bunazosin HCl, Doxazosin mesylate, Phenoxybenzamine HCl, Prazosin HCl, Terazosin HCl, Thymoxamine HCl, Tolazoline HCl Beta Blockers: Acebutolol HCl, Arotinolol HCl, Atenolol, Bevantolol HCl, Bisoprolol hemifumarate, CarteololHCl, Chlorthalidone, Cloranolol HCl, Metoprolol succinate, Metoprolol Tartrate, Nebivolol hydrochloride, Penbutolol sulfate, Pindolol, Propranolol HCl, S-atenolol, Sotalol HCl, Tertatolol Hydrochloride, Diuretics: Acetazolamide, Amiloride HCl, Azosemide, Bumetanide HCl, Chlorthalidone, D-mannitol, Furosemide, Hydrochlorothiazide, Indapamide, Metolazone, Piretanide, Spironolactone, Torasemide, Triamterene, Tripamide Vasodilators: Alprostadil, Alprostadil α-cyclodextrin, Diazoxide, Dilazep Dihydrochloride, Etofylline nicotinate, Hydralazine HCl, Iloprost, Isosorbide Dinitrate, Isosorbide Mononitrate, Isoxsuprine HCl, Kallikrein, Minoxidil, Molsidomine, Nafronyl oxalate, Nitroglycerin, Sodium nitroprusside, Verapamil HCl Calcium Channel Blockers: Amlodipine adipate, Amlodipine besylate, Amlodipine camsylate, Amlodipine maleate, Amlodipine mesylate monohydrate, Amlodipine nicotinate, Amlodipine orotate, Bepridil Hydrochloride, Cilnidipine, Diltiazem HCl, Efonidipine HCl, Felodipine, Gallopamil HCl, Isradipine, Lacidipine, Lercanidipine HCl, Manidipine HCl, Nicardipine HCl, Nicorandil, Nifedipine, Nilvadipine, Nimodipine, Nisoldipine, Nitrendipine, s-amlodipine adipate, S-Amlodipine besylate, s-amlodipine S-Amlodipine besylate gentisate, S-amlodipine S-Amlodipine besylate nicotinate, Verapamil HCl Angiotensin Converting Enzyme Inhibitors: Alacepril, Benazepril HCl, Captopril, Cilazapril, Delapril HCl, Enalapril maleate, Fosinopril sodium, Imidapril HCl, Lisinopril, Moexipril HCl, Perindopril tertrabutylamine, Quinapril, Ramipril, Spirapril HCl, Temocapril hydrochloride, Trandolapril, Zofenopril Calcium Nonselective α, β blocker: Amosulalol HCl, Carvedilol, Carvedilol, Labetalol HCl Vaccines: Live attenuated human rotavirus, Attenuated live varicella virus, Purified influenza virus antigen(inactivated), Absorbed Tetanus toxoid, Attenuated Japanese encephalitis virus, Attenuated live measles virus, Attenuated live rubella virus, Attenuated polio virus, Freeze-dried rabies vaccine, Freeze-dried glutamate BCG, Calmett-Guerin Strain, *Haemophilus influenzae*, Influenza virus hemagglutinin, Hepatitis A antigen, Hepatitis B Vaccine, Human anti-hepatitisB immunoglobulin, Inactivated Hantaan virus, Inactivated Japanese encephalitis virus, Inactivated *Leptospira* icterohaemorrhagiae strain, Inactivated polio virus, Live measles virus vaccine, Live *Salmonella typhi* strain, Live strain of *Bacillus Calmett-Guerin, Mycobatcerium bovis* (B.C.G), Purified influenza virus antigen(attenuated), Purified hepatitis B surface antigen, Purified hepatitis A antigen(inactivated), Purified polysaccharide from *Streptococcus pneumoniae*, Purified Vi capsular polysaccharide of *Salmonella typhi*, Tetanus antitoxin Immune Globulin: Humananti-hepatitis B immunoglobulin, Humananti-Tetanus immunoglobulin, Immunoglobulin anti-D(Rho), Immunoglobulin-G, Human cytomegalovirus immunoglobulin, Human varicella zoster immunoglobulin, Immunoglobulin, Immunoglobulin-M, Mamushi antivenom equine isophyllized, Rabies human immunoglobulin Other Biological Agents: Interferon alfacon-1

Miscellaneous GI Drugs: Balsalazide disodium, Camostat Mesylate, Dimethicone, Magnesium Hydroxide, Orlistat, Simethicone, Tegaserod hydrogen maleate Anorexiant: Phendimetrazine tartrate, Phentermine HCl, Sibutramine HCl Antiulcerants: Mesalazine, Revaprazan, Ecabet Sodium, Misoprostol, Oxyphencyclimine HCl, Pirenzepine HCl, Proglumide, Rebamipide, Sofalcone, Sucralfate, Teprenone, Tripotassium dicitrato bismuthate H2 Receptor Blockers: Cimetidine, Famotidine, Nizatidine, Ranitidine bismuth citrate, Ranitidine HCl, Roxatidine acetate HCl H+ Pump Inhibitors: Esomeprazol magnesium, Esomeprazole strontium tetrandyrate, Lansoprazole, Omeprazole, Omeprazole sodium, Pantoprazole sodium, Pantoprazole sodium sesquihydrate, Rabeprazole sodium Digestants: Alibendol, Magnesium dimecrotate, Pancrease, Pancreatin, Pancrelipase GI Tract Regulators & Antispasmodics: Aclatonium Napadisilate, Alverine citrate, Butropium Bromide, Caroverine, Caroverine HCl, Cisapride tartrate, Dicyclomine HCl, Difemerine HCl, Domperidone, Domperidone Maleate, Fenoverine, Itopride HCl, Levosulpiride, Mebeverine HCl, Metoclopramide HCl, Mosapride citrate, Octylonium Bromide, Scopolamine butylbromide, Tiropramide HCl, Trimebutine maleate, Trospium Chloride Medicines for intestinal disorders, Antidiarrheals: *Bacillus licheniformis, Bacillus polyfermenticus, Bacillus subtilis, Lactobacillus acidophillus, Saccharomyces cerevisiae* hansen CBS, Dioctahedralsmectite, Loperamide HCl, Loperamide oxide monohydrate, Nifuroxazide Laxatives, Purgatives: Bisacodyl, Magnesium Oxide, Sodium Picosulfate Antiemetics: Aprepitant, Azasetron HCl, Dolasetron mesilate, Ondansetron, Palonosetron HCl, Prochlorperazine, Ramosetron HCl, Trimethobenzamide HCl Cholelitholitics & Hepatic Protectors: Arginine HCl, Cyanocobalamin, L-cysteine, L-glutathione, L-Ornithine-L-Aspartate, Silymarin, Taurine, Tocopherol Acetate, UrsodesoxycholicAcid Female hormone drugs: Clomiphene Citrate, Drospirenone, Estradiol, Estradiol hemihydrate, Estradiol valerate, Estrogens, Ethynyl estradiol, Etonogestrel, Medroxyprogesterone Acetate, Norethisterone, Norgestimate, Progesterone Bone metabolism agents: Alendronate sodium, Disodium Etidronate, Ibandronate sodium, Ibandronic acid monosodium salt monohydrate, Ossopansubstance, Pamidronate Disodium, Raloxifene HCl, Risedronatesodium, Zoledronic acid Androgens, anabolic steroids: Danazol, Methyltestosterone, Oxandrolone, Oxymetholone, Testosterone Adrenal corticosteroides: Deflazacort, Dexamethasone, Dexamethasone sodium phosphate, Dexamethasone palmitate, Hydrocortisone, Hydrocortisone sodium succinate, Methylprednisolone, MethylPrednisolone acetate, MethylPrednisolone sodium succinate, Mometasone furoate, Mometasone furoate monohydrate, Norepinephrine Bitartrate, Prednisolone, Prednisolone acetate, Prednisolone sodium succinate, Prednisolone stearylglycolate, Triamcinolone, Triamcinolone acetonide, Betamethasone sodium phosphate Other Hormone & Synthetic Agents: Desmopressin acetate, Exenatide, Lanreotideacetate, Laronidase, Octreotide, Octreotide Acetate, Thioctic Acid(α-lipoicacid), Triptorelin acetate, Levonorgestrel Insulins: Human insulin, Insulin aspart, Insulin bovine, Insulin detemir, Insulin glargine, Insulin glulisine, Insulin lispro, Pork insulin Oral Hypoglycemic Agents: Acarbose, Glibenclamide, Gliclazide, Glimepiride, Metformin HCl, Glyburide, Nateglinide, Pioglitazone HCl, Repaglinide, Rosiglitazone maleate, Sitagliptin phosphate monohydrate, Vildagliptin Gonadotropins: Buserelin acetate, Follitropin, Leuprolide acetate Thyroid hormones and related agents: Levothyroxine Sodium, Liothyronine Sodium Antithyroid Agents: Cinacalcet HCl, Methimazole, Propylthiouracil Antihistamines & antiallergics: Azelastine HCl, Bepotastinebesilate, Cetirizine HCl, Desloratadine, Dimenhydrinate, Ebastine, Emedastine Difumarate, Epinastine HCl, Fexofenadine, Fexofenadine HCl, Filgrastim, Hydroxyzine HCl, Ketotifen Fumarate, Levocetirizine HCl, Loratadine, Mequitazine, Olopatadine, Oxatomide, Pegfilgrastim, Piprinhydrinate, Terfenadine, Fluticasone furoate, Levocabastine HCl, Phenylephrine HCl, Pseudoephedrine HCl, Xylometazoline HCl Immunosuppressants: Cyclosporin, Everolimus, Infliximab, Mizoribine, Muromonab-CD3, Mycophenolic acid, Mycophenolate mofetil, Mycophenolate mofetil HCl, Palivizumab, Sirolimus, Tacrolimus, Tacrolimus hydrate Other immune related agents: Pidotimod, Thymomodulin General Anesthetics: Enflurane, Etomidate, Isoflurane, Ketamine HCl, Propofol, Sevoflurane CNS Stimulants: Atomoxetine HCl, Dexmethylphenidate, Methylphenidate HCl, Modafinil Antiparkinsonian Agents: Amantadine HCl, Bromocriptine Mesylate, Entacapone, Levodopa, Pramipexole dihydrochloride, Ropinirole HCl, Selegiline HCl, Tetrabenazine, Trihexyphenidyl HCl Nootropics & Neurotonics: Acetyl-1-carnitine HCl, CholineAlfoscerate, Donepezil HCl, Galantamine hydrobromide, Oxiracetam, Piracetam, Rivastigmine, Rivastigmine Tartrate Arthritis therapeutic & Antirheumatic Agents: Adalimumab, Auranofin, Chondroitin Sodium Sulfate, Diacerhein, Emorfazone, Etanercept, Glucosamine sulfate, Leflunomide, Pelubiprofen, S-Adenosyl-L-Methionine-Sulfate-p-Toluensulfonate, Sodium Hyaluronate Skeletal Muscle Relaxants: Afloqualone, Chlorphenesin Carbamate, Cisatracurium besylatel, Clostridium Botulinum A Toxin, Cyclobenzaprin HCl, Dantrolene Sodium, Gallaminetriethiodide, Methocarbamol, Orphenadrine Citrate, Orphenadrine HCl, Pancuronium Bromide, Pridinol Mesylate, Rocuronium Bromide, Succinylcholine Chloride, Thiocolchicoside, Tizanidine HCl, Tolperisone HCl, Vecuronium bromide Antiinflammatory Enzymes: Chymopapain, Lysozyme Chloride, Pronase, Semialkaline Protease, Serratiopeptidase Gout Preparations: Allopurinol, Colchicine, Probenecid, Rasburicase Other Neuromuscular System: Memantine HCl, Naloxone HCl, Tacrin Local Anesthetics Bupivacaine HCl, Lidocaine, Lidocaine HCl, Proparacaine HCl, Ropivacaine, Ropivacaine HCl Neuromuscular Disorder related drugs: Acamprosate, Pyridostigmine Bromide, Riluzole Narcotics: Buprenorphine HCl, Codeine phosphate, Fentanyl, Fentanyl citrate, Hydrocodone bitartrate, Hydromorphone HCl, Morphine HCl, Morphine Sulfate, Nalbuphine HCl, Oxycodone HCl, Oxycodone terephtalate, Pethidine HCl, Propoxyphene HCl, Remifentanyl HCl NSAIDs (Nonsteroidal Anti-Inflammatory Drugs): Celecoxib, Acetaminophen, Clonixin lysinate, Diclofenac sodium, Ibuprofen, Ketoprofen, Ketorolac Tromethamine, Naproxen sodium, Naratriptan HCl, Tramadol HCl, Zolmitriptan Anticonvulsants: Carbamazepine, Clonazepam, Diazepam, Gabapentin, Lamotrigine, Levetiracetam, Lorazepam, Magnesium valproate, Oxcarbazepine, Phenyloin, Phenyloin sodium, Pregabalin, Primidone, Sodium valproate, Topiramate, ValproicAcid, Vigabatrin, Zonisamide Hypnotics & Sedatives, major tranquilizer & Antipsychotics: Alprazolam, Amisulpride, Aripiprazole, Bromperidol, Haloperidol, Haloperidol decanoate, Levomepromazine maleate, Loxapine, Mesoridazine Besylate, Molindone HCl, Nemonapride, Olanzapine, Paliperidone, Perphenazine, Pimozide, Quetiapinefumarate, Risperidone, Sulpiride, Thioridazine HCl, Thiothixene, TiaprideHCl, Trifluoperazine HCl, Ziprasidone HCl monohydrate, Zolpidem tartrate, Zotepine Antidepressants: Moclobemide, Toloxatone, Amitriptyline HCl, ClomipramineHCl, Dothiepin HCl, Doxepin HCl, Imipramine HCl, Maprotiline HCl, Mianserine HCl, Nortriptyline HCl, Quinupramine, Citalopram HBr, Duloxetine HCl, Escitalopram oxalate, Fluoxetine HCl, Fluvoxamine maleate, Paroxetine HCl, Sertraline HCl, Bupropion HCl, Mirtazapine, Nefazodone HCl, Sodiumtianeptine, Trazodone HCl, Venlafaxine HCl Respiratory Stimulants: Doxapram HCl monohydrate, Poractant alfa Respiratory Relaxants: Aminophylline, Bambuterol HCl, Fluticasone Propionate, Ipratropium Bromide, Isoproterenol HCl, Tiotropium Bromide Monohydrate, Procaterol HCl, Salbutamol (Albuterol), Salbutamol sulfate, Salmeterol, Terbutaline Sulfate, Tulobuterol, Tulobuterol HCl, Beclomethasone Dipropionate, Budesonide, Ciclesonide, Formoterol fumarate, Formoterol fumarate dihydrate, Sodium cromoglycate Cough & Cold remedies: Acebrophylline, Acetylcysteine, AmbroxolHCl, Benzonatate, Bromhexine HCl, Dextromethorphan HBr, Doxofylline, Erdosteine, Letosteine, Levodropropizine, Mesna, Methyl N,S diacetylcysteinate, Nedocromil Sodium, S-carboxymethylcysteine, Sobrerol, ThenothiolaSodium, Theophylline Other Respiratory & Nasal Drugs: Omalizumab Leukotriene modulator: Montelukast sodium, Pranlukast hydrate, Zafirlukast Genitourinary Smooth Muscle Relaxants: Fesoterodine fumarate, Flavoxate HCl, Oxybutynin Chloride, Oxybutynin HCl, Propiverine HCl, Solifenacin succinate, Tolterodine l-tartrate Uterus Constrictors: Dinoprostone, Oxytocin Prostatitis/prostatic hypertrophy related agents: Alfuzosin HCl, Allylestrenol, Chlormadinone Acetate, Dutasteride, Finasteride, Tamsulosin HCl Drug for impotence therapy: Alprostadil, Mirodenafil HCl, Sildenafil citrate, Tadalafil, Udenafil, Vardenafil HCl Other Genito-Urinary Drugs: Bethanechol Chloride, Nitrofurantoin, Pentosan polysulfate sodium, Ritodrine HCl In order to adjust the physicochemical properties of a physiological active substance as a solid solute used as a solute for the present invention, a pharmaceutically acceptable additive may be additionally used, and examples of the additive include at least one mixture selected from the group including hydroperoxy methylcellulose (currently known as hypromellose), hydroxypropyl cellulose, polyvinyl pyrrolidone, polyethylene glycol, sodium lauryl sulphate, dioctyl sulfosuccinate, gelatin, casein, lecithin (phosphatide), textran, gum acacia, cholesterol, tragacanth, stearic acid, benzalkonium chloride, calcium stearate, glycerol monostearate, cetostearyl alcohol, cetomacrogol emulsified wax, sorbitan ester, polyoxyethylene alkyl ether (e.g. macrogol ether, cetomacrogol 1000), polyoxyethylene castor oil derivative, polyoxyethylene sorbitan fatty acid ester (e.g. commercially available Tweens (registered trade mark), tween 20 (registered trade mark) and tween 80(registered trade mark) (ICI Speciality Chemicals)), polyethylene glycol (e.g. Carbowaxs 3550 (registered trade mark) and 934 (registered trade mark) (Union Carbide)), polyoxyethylene stearate, colloidal silicon dioxide, phosphate, carboxymethylcellulose, calcium, carboxymethylcellulose sodium, methylcellulose, hydroxyethylcellulose, hypromellose phthalate, amorphous cellulose, magnesium aluminium silicate, triethanolamine, polyvinyl alcohol(PVA), 4-(1,1,3,3-tetramethylbutyl)-phenolic polymer having ethylene oxide and formaldehyde (also known as tyloxapol, superion and tritone), poloxamer (e.g. Pluronics F68(registered trade mark) and F108(registered trade mark), block copolymer of ethylene oxide and propylene oxide), poloxamine (e.g. known as Tetronic 908(registered trade mark), poloxamine 908(registered trade mark)), tetrafunctional block copolymer derived by sequentially adding propylene oxide and ethylene oxide to ethylenediamine (BASF Wyandotte Corporation, in Parsippany N.J.), tetronic 1508 (registered trade mark, T-1508, (BASF Wyandotte Corporation), alkyl aryl polyether sulfonate (e.g. triton X-200(registered trade mark), Rohm and Haas), a mixture of sucrose stearate and sucrose distearate (e.g., Crodestas F-110(registered trade mark, Croda Inc.), p-isononylphenoxypoly-(glycidol) (known as Olin-IOG(registered trade mark) or surfactant 10-G(registered trade mark) (Olin Chemicals, Connecticut Stamford)), crodestas SL-40(registered trade mark, Croda Incorporation), and $C_{18}H_{37}CH_2(CON(CH_3)-CH_2(CHOH)_4(CH_2OH)_2$ (SA90HCO, Eastman Kodak Co.), decanoyl-N-methylglucamide, n-decylβ-D-glucopyranoside, n-decyl-β-D-maltopyranoside, n-dodecyl-β-D-glucopyranoside, n-dodecylβ-D-maltoside, heptanoyl-N-methylglucamide, n-heptyl-β-D-glucopyranoside, n-heptylβ-D-thioglucoside, n-hexylβ-D-thioglucoside, nonanoyl-N-methylglucamide, n-noylβ-D-glucopyranoside, octanoyl-N-methylglucamide, n-octyl-β-D-glucopyranoside, octyl-β-D-thioglucopyranoside, PEG-phospholipid, PEG-cholesterol, PEG-cholesterol derivative, PEG-vitamin A, PEG-vitamin E, PEG derived vitamin E (vitamin E TPGS(registered trademark, Eastman Kodak Corp)), lysozyme, vinylpyrrolidone, various polymers meeting USFDA standard of GRAS(generally recognized as safe) such as any copolymer of vinylacetate, low molecular weight oligomer, natural products and nonionic/anionic/cationic/amphoteric surfactants.

Furthermore, known pharmaceutical additives may be additionally used, and are mostly disclosed in [Handbook of Pharmaceutical Excipients] laid open by American Pharmaceutical Association and The Pharmaceutical Society of Great Britain, which is specially referred in the present invention.

Unlike conventional processes, in the present invention, in a particle formation step, heated compressed gas is sprayed together with a mixture of a compressed fluid and a liquid solution, thereby facilitating material transfer by the heated compressed gas. Therefore, it is possible to prepare powder with more fine and more uniform distribution. The heated compressed gas includes at least one material selected from the group including air, nitrogen, and argon, and may have a temperature ranging from 30 to 120° C. and a pressure ranging from 50 to 1000 kPa.

The present invention is characterized in that in order to prepare ultra-fine particles with uniform particle size distribution, heated compressed gas is sprayed together with a single-phase or colloidal mixture including a compressed fluid and a liquid solution. For this operation, a multiple-fluid nozzle for two or more fluids, such as a multiple-fluid coaxial nozzle, may be employed. The nozzle is capable of spraying a single-phase or colloidal mixture including a compressed fluid and a liquid solution, together with heated compressed gas, at a spray outflow part, which allows the mixture to contact with the heated compressed gas.

In the present invention, a drying gas is one material selected from the group including air, nitrogen, and argon, heated up to a temperature ranging from 20 to 300° C., and is preferably air heated up to a temperature ranging form 100 to 150° C. Also, the flow rate of drying gas may be within a range of 0.1 to 10.0 m$^3$/min, preferably within a range of 0.2 to 5.0 m$^3$/min.

In the present invention, a mixing unit indicates a pressure vessel made from metal, ceramic, reinforced glass, copper, which is filled with filler or is mounted with a stirrer, and is for maximizing the contact area of a liquid solvent and a compressed fluid and thereby efficiently mixing the two materials.

In the present invention, the injection velocity ratio of the compressed fluid to the liquid solution (injection velocity of compressed fluid/injection velocity of liquid solution) may be within a range of 0.1 to 50, preferably of 1 to 3, more preferably of 1.5 to 2.5.

Collecting the ultra-fine particles prepared in the present invention may be carried out by any one of conventional dust-collecting devices, such as a metal or polymer filter/net, a dust-collecting cyclone using air stream, or the like.

As described above, according the present invention, through the method using a compressed fluid, it is possible to prepare fine particles and fine particle compositions of various compounds, with an average particle size of 0.2 to 3 micron, in which 90% or more of the particles have a size of less than 3 micron.

Also, the particle preparation method according to the present invention uses heated compressed gas in a particle forming step, which makes it possible to prepare ultra-fine particles with highly uniform particle size distribution.

EFFECT OF THE INVENTION

As described above, according the present invention, through the method using a compressed fluid, it is possible to prepare fine particles and fine particle compositions of various compounds, with an average particle size of 0.2 to 3 micron, in which 90% or more of the particles have a size of less than 3 micron.

Also, the particle preparation method according to the present invention uses heated compressed gas in a particle forming step, which makes it possible to prepare ultra-fine particles with highly uniform particle size distribution.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENT

Hereinafter, the present invention will be described with reference to Examples. However, the examples are illustrative only, and are not intended to limit the scope of the present invention.

Examples 1 to 9

Preparation of Cyclosporine Ultra-Fine Particles

Figure 1:
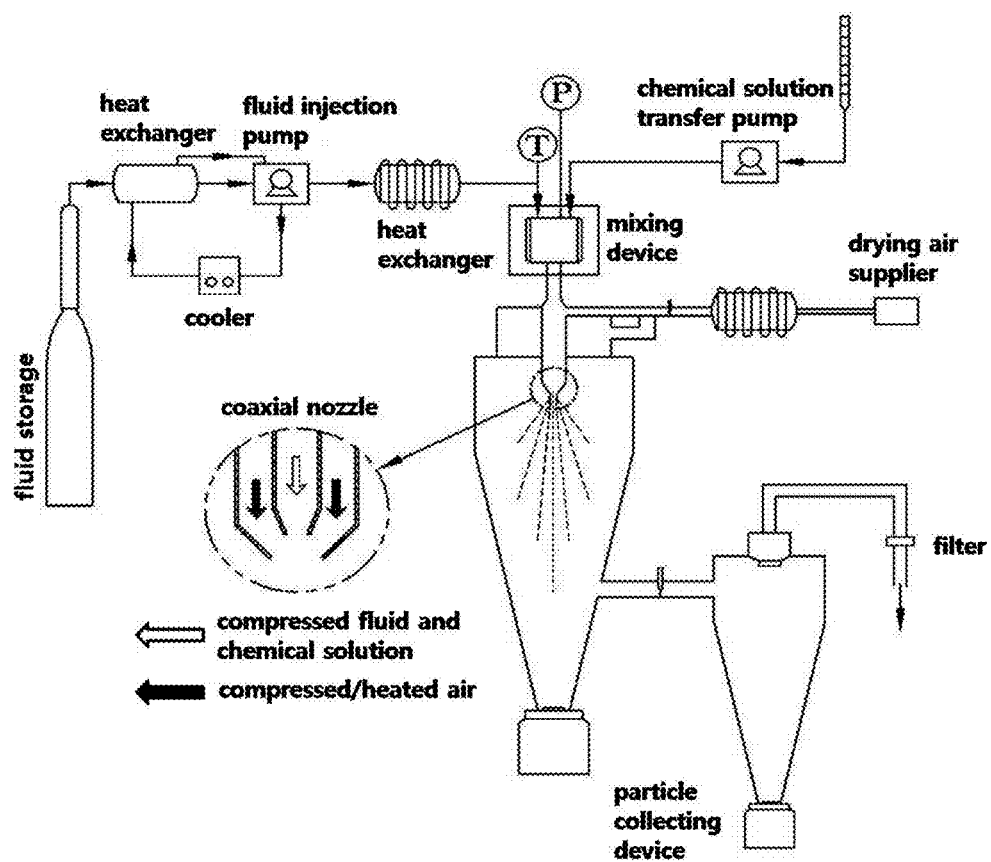
FIG. 1 is a mimetic diagram illustrating a method and apparatus for preparing ultra-fine particles with uniform particle size distribution, according to one embodiment of the present invention.
Figure 2:
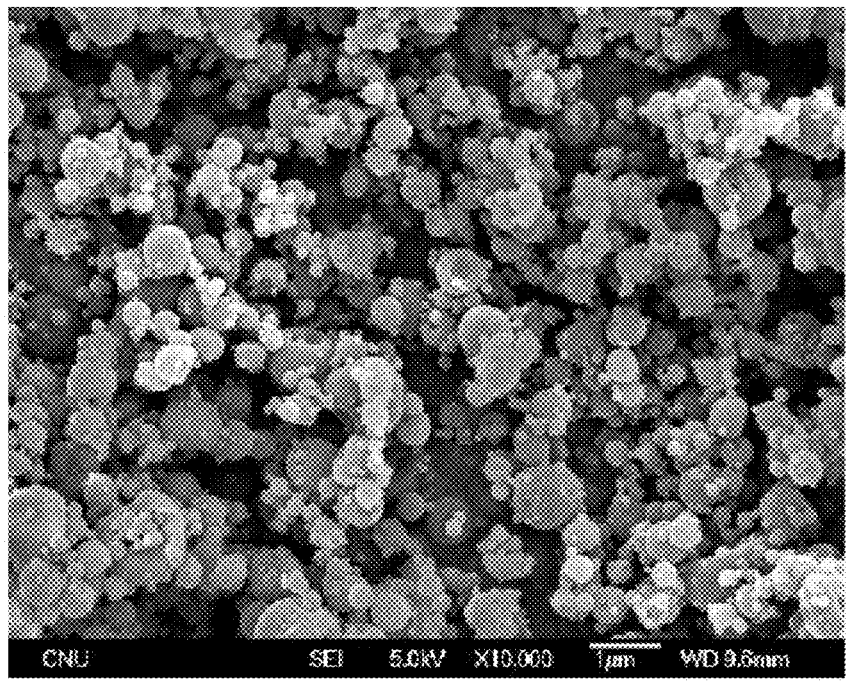
FIG. 2-9 are an analysis result of a scanning electron microscope on particles obtained from Example 3, 4, 9, 12, 14, 20, 26 and 32.
Figure 3:
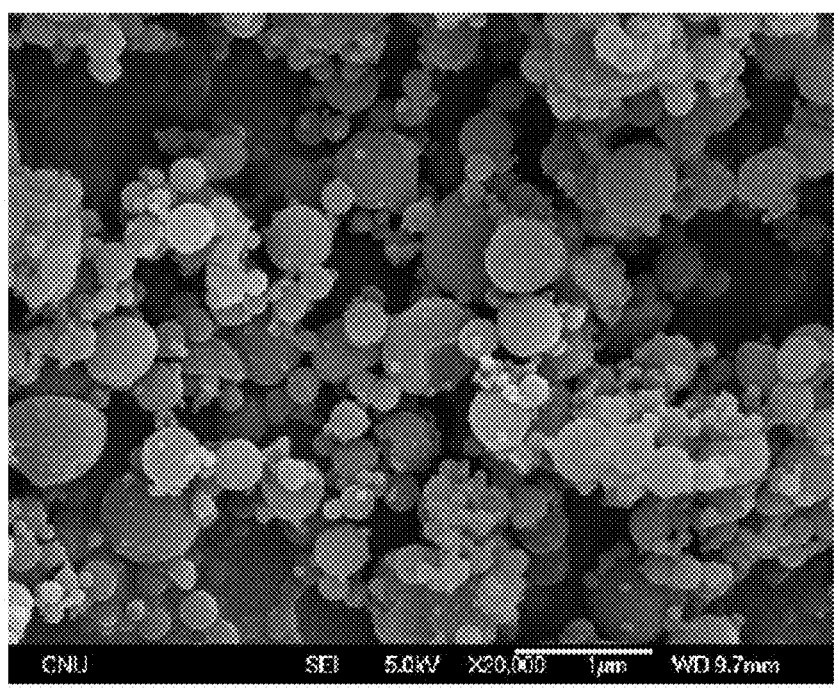
Figure 4:
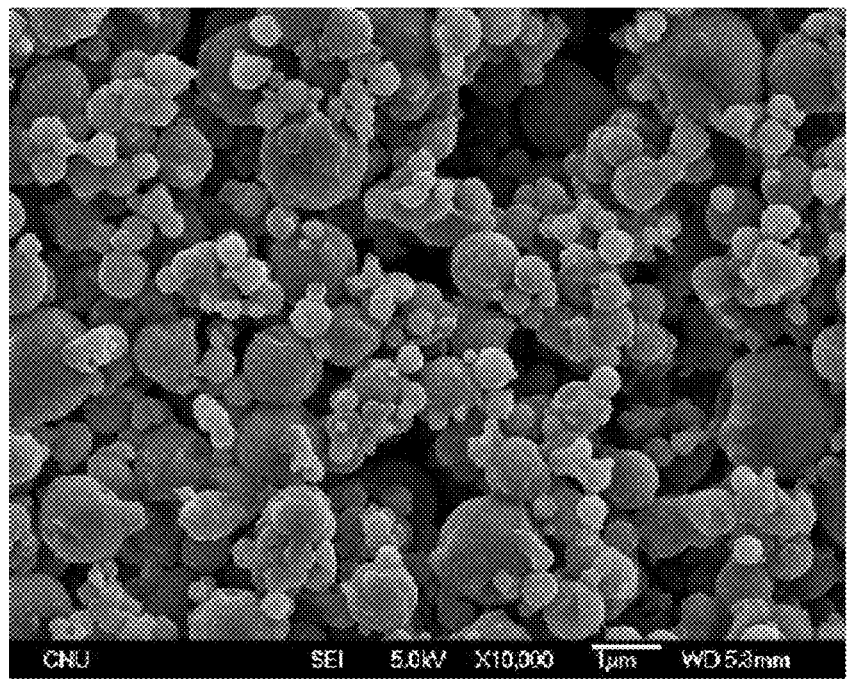

Cyclosporine ultra-fine particles were prepared by using a particle preparation process according to the present invention. First, cyclosporine was dissolved in ethanol in the concentration of 30 mg/l. Previously compressed/heated carbon dioxide (or mixture of carbon dioxide and ether, or mixture of carbon dioxide and fluorinated hydrocarbon (R-22, chlorodifluoromethane)) and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. Examples 1 to 9 were carried out at 45° C. and 82 bar. The injection amounts of compressed fluid and chemical solution preferably range from 1 to 50 g/min and from 1 to 30 g/min, respectively. Moreover, the ratio of the compressed fluid and the chemical solution is preferably 1-3. Also, the inside hole size of the coaxial nozzle ranges from 1 to 500 μm, and preferably is 100 μm. Drying air was used at a flow rate of 0.2 to 0.4 m$^3$/min and a temperature of 120 to 150° C. The process conditions and prepared particles' sizes of Examples 1 to 9 are noted in Table 1. The particle size was measured by using dynamic light scattering and laser diffraction particle size analysis. In order to check the particles prepared according to the present invention, particles obtained from Examples 3, 4, and 9 were observed by using a scanning electron microscope. The results are shown in FIGS. 2 to 4.

TABLE 1

| Exp | Injection rate of compressed fluid | Injection rate of chemical solution | Pressure and temp. of heated/ compressed gas | Average particle size (dynamic light scattering) | Laser diffraction particle size analysis (on volume base) | | | |
|---|---|---|---|---|---|---|---|---|
| | | | | | D10% | D50% | D90% | SPAN |
| 1 | CO$_2$-40 g/min | 18 g/min | 100 KPa, 40° C. | 550.2 nm | 0.51 μm | 0.88 μm | 2.11 μm | 1.8 |
| 2 | CO$_2$-40 g/min | 18 g/min | 100 KPa, 80° C. | 535.4 nm | 0.41 μm | 0.76 μm | 1.91 μm | 2.0 |
| 3 | CO$_2$-40 g/min | 18 g/min | 200 KPa, 40° C. | 510.2 nm | 0.39 μm | 0.77 μm | 1.71 μm | 1.7 |
| 4 | CO$_2$-40 g/min | 18 g/min | 200 kPa, 80° C. | 490.5 nm | 0.32 μm | 0.73 μm | 1.75 μm | 2.0 |
| 5 | CO$_2$-40 g/min | 12 g/min | 100 KPa, 40° C. | 399.2 nm | 0.35 μm | 0.66 μm | 1.46 μm | 1.7 |
| 6 | CO$_2$-40 g/min | 15 g/min | 200 KPa, 40° C. | 470.2 nm | 0.31 μm | 0.71 μm | 1.55 μm | 1.7 |
| 7 | CO$_2$-35 g/min R-22-5 g/min | 18 g/min | 300 KPa, 120° C. | 486.7 nm | 0.33 μm | 0.71 μm | 1.64 μm | 1.8 |

TABLE 1-continued

| Exp | Injection rate of compressed fluid | Injection rate of chemical solution | Pressure and temp. of heated/ compressed gas | Average particle size (dynamic light scattering) | Laser diffraction particle size analysis (on volume base) | | | |
|---|---|---|---|---|---|---|---|---|
| | | | | | D10% | D50% | D90% | SPAN |
| 8 | CO$_2$-30 g/min Dimethylether-10 g/min | 18 g/min | 500 KPa, 120° C. | 453.8 nm | 0.37 μm | 0.75 μm | 1.69 μm | 1.8 |
| 9 | CO$_2$-40 g/min | 18 g/min | none | 958.6 nm | 0.65 μm | 1.12 μm | 3.83 μm | 2.8 |

As noted in Table 1, cyclosporine particles prepared according to Examples 1 to 8 have an average particle size ranging from 399.2 to 550.2 nm. Also, 90% or more of the particles obtained from Examples 1 to 8 have a size of less than 3 μm. Also, as noted in Table 1, as the pressure and temperature of the heated compressed gas injected through the outside hole of the coaxial nozzle increased, the average particle size of the prepared particles decreased, and the particle size distribution also became uniform. Thus, the introduction of such heated compressed gas facilitates material transfer during particle formation, thereby generating uniform nano-unit ultra-fine particles. This is more obvious when compared to the case where the heated compressed gas was not used in Example 9. Also, as shown in the drawings, it can be seen that in the particles obtained without the heated compressed gas (Example 9), many micro-unit particles exist, while in the particles obtained by using the heated compressed gas (Examples 3 and 4), nano-unit fine particles were prepared.

Examples 10 to 17

Preparation of Cilostazol Ultra-Fine Particles

Figure 5:
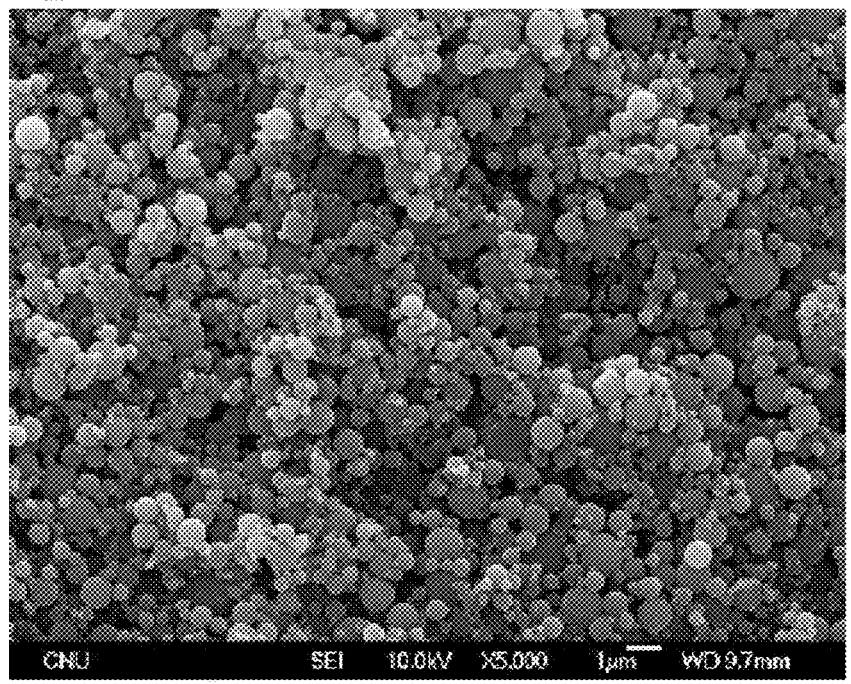
Figure 6:
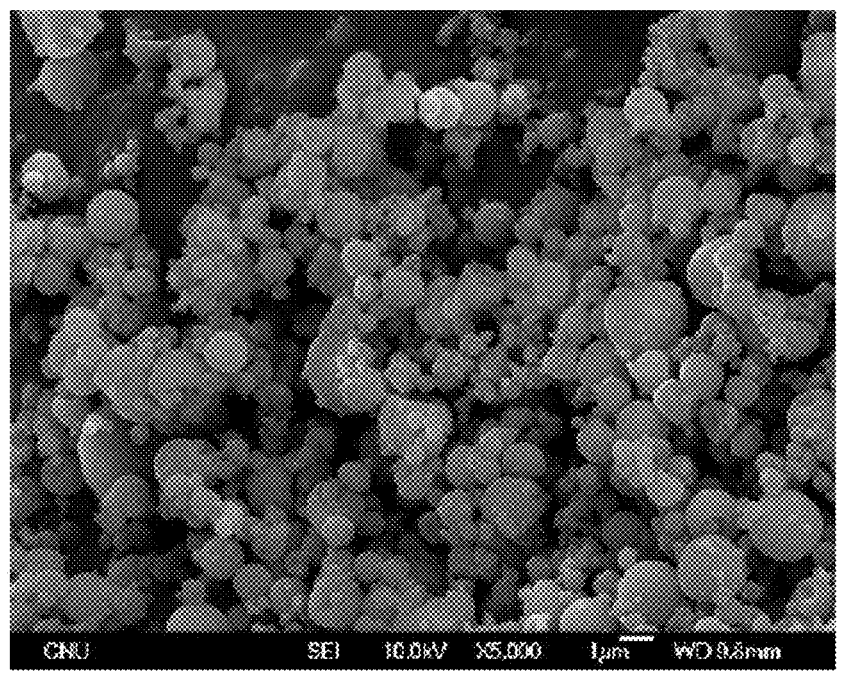

Cilostazol ultra-fine particles were prepared by using a particle preparation process according to the present invention. First, cilostazol was dissolved in acetic acid or methylene chloride in the concentration of 50 mg/ml. Previously compressed/heated carbon dioxide (or mixture of carbon dioxide and ether, or mixture of carbon dioxide and fluorinated hydrocarbon (R-22, chlorodifluoromethane)) and the prepared solution were injected at a predetermined flow velocity and mixed, and then sprayed through the inside hole of a coaxial nozzle. Herein, the temperature and pressure range from 30 to 90° C. and from 60 to 300 bar, preferably from 40 to 80° C. and from 75 to 120 bar, respectively. Examples 10 to 14 used acetic acid as a solvent, and were carried out at 70° C., and 95 bar. Examples 15 to 17 used methylene chloride, and were carried at 40° C. and 82 bar. The injection amounts of compressed fluid and chemical solution preferably range from 1 to 50 g/min and from 1 to 30 g/min, respectively. Moreover, the ratio of the compressed fluid and the chemical solution is preferably 1-3. Also, the inside hole size of the coaxial nozzle ranges from 1 to 500 μm, and preferably is 100 μm. Drying air was used at a flow rate of 0.2 to 0.4 m$^3$/min and a temperature of 120 to 160° C. The process conditions and prepared particles' sizes of Examples 10 to 17 are noted in Table 2. The particle size was measured by using dynamic light scattering and laser diffraction particle size analysis. In order to check the particles prepared according to the present invention, particles obtained from Examples 12 and 14 were observed by using a scanning electron microscope. The results are shown in FIGS. 5 and 6.

TABLE 2

| Exp | Injection rate of compressed fluid | Injection rate of chemical solution | Pressure and temp. of heated/ compressed gas | Average particle size (dynamic light scattering) | Laser diffraction particle size analysis (on volume base) | | | |
|---|---|---|---|---|---|---|---|---|
| | | | | | D10% | D50% | D90% | SPAN |
| 10 | CO$_2$-40 g/min | 15 g/min | 100 KPa, 40° C. | 515.6 nm | 0.50 μm | 0.89 μm | 2.02 μm | 1.7 |
| 11 | CO$_2$-40 g/min | 15 g/min | 100 KPa, 80° C. | 505.2 nm | 0.49 μm | 0.81 μm | 1.95 μm | 1.8 |
| 12 | CO$_2$-40 g/min | 15 g/min | 200 KPa, 80° C. | 450.5 nm | 0.42 μm | 0.79 μm | 2.05 μm | 2.1 |
| 13 | CO$_2$-35 g/min R-22-5 g/min | 15 g/min | 400 KPa, 120° C. | 432.8 nm | 0.39 μm | 0.74 μm | 1.87 μm | 2.0 |
| 14 | CO$_2$-40 g/min | 15 g/min | none | 962.5 nm | 0.66 μm | 1.21 μm | 3.94 μm | 2.7 |
| 15 | CO$_2$-40 g/min | 18 g/min | 200 KPa, 40° C. | 435.6 nm | 0.39 μm | 0.85 μm | 1.92 μm | 1.8 |
| 16 | CO$_2$-35 g/min R-22-5 g/min | 18 g/min | 500 KPa, 80° C. | 423.1 nm | 0.40 μm | 0.81 μm | 1.79 μm | 1.7 |
| 17 | CO$_2$-40 g/min | 18 g/min | none | 812.2 nm | 0.61 μm | 1.25 μm | 3.75 μm | 2.5 |

As noted in Table 2, cilostazol particles prepared according to Examples 10 to 17 have an average particle size ranging from 515.6 to 962.5 nm. Also, 90% or more of the particles obtained from Examples 10 to 13 and 15 and 16 have a size of less than 3 μm. Also, as noted in Table 2, as the pressure and temperature of the heated compressed gas injected through the outside hole of the coaxial nozzle increased, the average particle size of the prepared particles decreased, and the particle size distribution also became uniform. Thus, the introduction of such heated compressed gas facilitates material transfer during particle formation, thereby generating uniform nano-unit ultra-fine particles. This is more obvious when compared to the case where the heated compressed gas was not used in Examples 14 and 17.

Examples 18 to 22

Preparation of Dutasteride Ultra-Fine Particles

Figure 7:
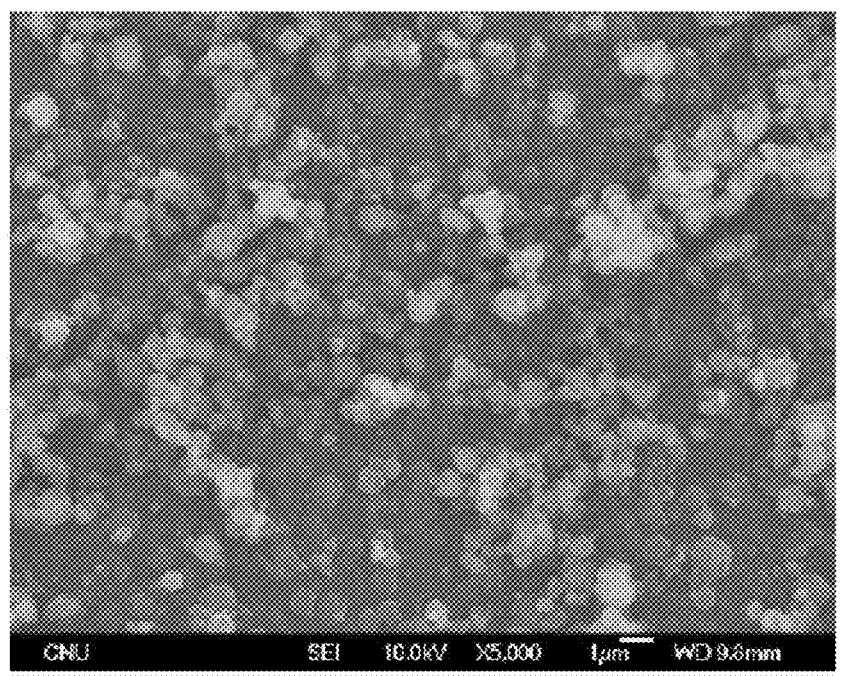

Dutasteride ultra-fine particles were prepared by using a particle preparation process according to the present invention. First, dutasteride was dissolved in acetic acid or methylene chloride in the concentration of 50 mg/ml. Previously compressed/heated carbon dioxide (or mixture of carbon dioxide and ether, or mixture of carbon dioxide and fluorinated hydrocarbon (R-22)) and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. Examples 17 to 21 were carried out at 45° C. and 82 bar. The injection amounts of compressed fluid and chemical solution preferably range from 1 to 50 g/min and from 1 to 30 g/min, respectively. Moreover, the ratio of the compressed fluid and the chemical solution is preferably 1-3. Also, the inside hole size of the coaxial nozzle ranges from 1 to 500 µm, and preferably is 100 µm. Drying air was used at a flow rate of 0.2 to 0.4 m³/min and a temperature of 120 to 150° C. The process conditions and prepared particles' sizes of Examples 17 to 21 are noted in Table 3. The particle size was measured by using dynamic light scattering and laser diffraction particle size analysis. In order to check the particles prepared according to the present invention, particles obtained from Example 20 were observed by using a scanning electron microscope. The results are shown in FIG. 7.

As noted in Table 3, dutasteride particles prepared according to Examples 18 to 22 have an average particle size ranging from 402.2 to 550.2 nm. Also, 90% or more of the particles obtained from Examples 18 to 22 have a size of less than 3 µm.

Examples 23 to 25

Preparation of Megestrol Acetate Ultra-Fine Particles

Megestrol acetate ultra-fine particles were prepared by using a particle preparation process according to the present invention. First, megestrol was dissolved in acetate acetone. Previously compressed/heated carbon dioxide and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. The injection amounts of carbon dioxide and chemical solution preferably range from 1 to 50 g/min and from 1 to 30 g/min, respectively. Moreover, the ratio of carbon dioxide and the chemical solution is preferably 1-3. Examples 23 to 25 were carried out at 45° C., and 82 bar, with carbon dioxide and chemical solution in amounts of 40 g/min and 15 g/min. Also, the inside hole size of the coaxial nozzle ranges from 1 to 500 µm, and preferably is 100 µm. Drying air was used at a flow rate of 0.2 to 0.4 m³/min and a temperature of 120 to 150° C. The process conditions and prepared particles' sizes of Examples 23 to 25 are noted in Table 4. The particle size was measured by using dynamic light scattering and laser diffraction particle size analysis.

TABLE 3

| Exp | Injection rate of compressed fluid | Injection rate of chemical solution | Pressure and temp. of heated/compressed gas | Average particle size (dynamic light scattering) | Laser diffraction particle size analysis (on volume base) | | | |
|---|---|---|---|---|---|---|---|---|
| | | | | | D10% | D50% | D90% | SPAN |
| 18 | $CO_2$-40 g/min | 12 g/min | 200 KPa, 40° C. | 402.2 nm | 0.35 µm | 0.61 µm | 1.23 µm | 1.4 |
| 19 | $CO_2$-40 g/min | 15 g/min | 200 KPa, 40° C. | 465.5 nm | 0.39 µm | 0.69 µm | 1.42 µm | 1.5 |
| 20 | $CO_2$-40 g/min | 18 g/min | 200 KPa, 40° C. | 550.2 nm | 0.45 µm | 0.79 µm | 1.91 µm | 1.8 |
| 21 | $CO_2$-35 g/min Dimethylether-5 g/min | 18 g/min | 350 KPa, 80° C. | 541.3 nm | 0.47 µm | 0.77 µm | 1.83 µm | 1.8 |
| 22 | $CO_2$-30 g/min Dimethylether-10 g/min | 18 g/min | 500 KPa, 120° C. | 524.3 nm | 0.41 µm | 0.73 µm | 1.77 µm | 1.9 |

TABLE 4

| Exp | Injection rate of compressed fluid | Injection rate of chemical solution | Solution concentration | Pressure and temp. of heated/compressed gas | Average particle size (dynamic light scattering) | Laser diffraction particle size analysis (on volume) | | | |
|---|---|---|---|---|---|---|---|---|---|
| | | | | | | D10% | D50% | D90% | SPAN |
| 23 | $CO_2$-40 g/min | 15 g/min | 5 mg/Ml | 200 KPa, 40° C. | 395.5 nm | 0.33 µm | 0.62 µm | 1.18 µm | 1.4 |
| 24 | $CO_2$-40 g/min | 15 g/min | 10 mg/Ml | 200 KPa, 40° C. | 462.4 nm | 0.43 µm | 0.69 µm | 1.46 µm | 1.5 |
| 25 | $CO_2$-40 g/min | 15 g/min | 20 mg/Ml | 200 KPa, 40° C. | 593.2 nm | 0.56 µm | 0.81 µm | 2.01 µm | 1.8 |

As noted in Table 4, megestrol acetate particles prepared according to Example 23 have an average particle size of 395.5 nm. Also, 90% or more of the particles obtained from Examples 23 to 25 have a size of less than 3 μm.

Examples 26 to 28

Preparation of Lysozyme Ultra-Fine Particles

Figure 8:
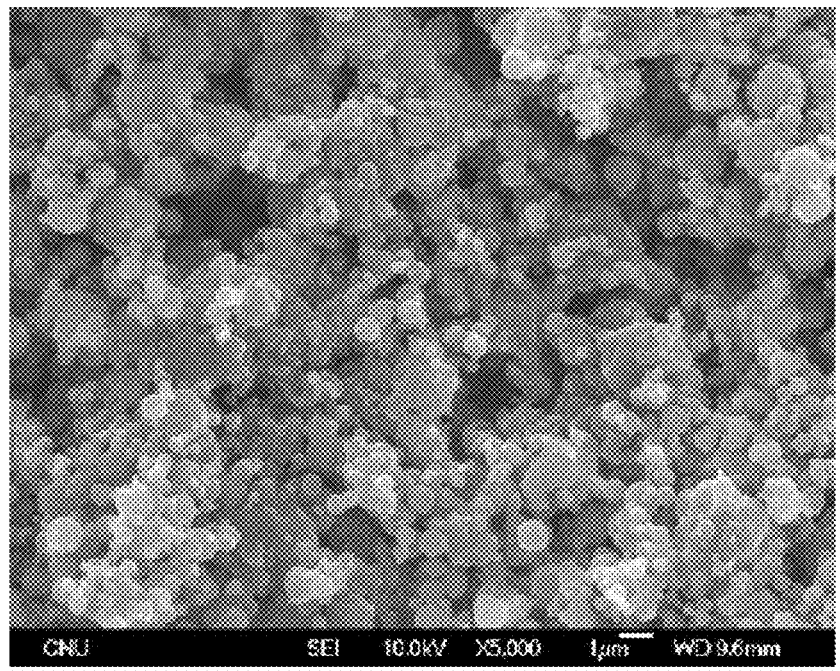

Lysozyme ultra-fine particles were prepared by using a particle preparation process according to the present invention. First, lysozyme was dissolved in water. Previously compressed/heated carbon dioxide and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. The injection amounts of carbon dioxide and chemical solution preferably range from 1 to 50 g/min and from 1 to 30 g/min, respectively. Moreover, the ratio of the carbon dioxide and the chemical solution is preferably 1-3. Examples 26 to 28 were carried out at 70° C., and 96 bar, with carbon dioxide and chemical solution in amounts of 40 g/min and 15 g/min. Also, the inside hole size of the coaxial nozzle ranges from 1 to 500 μm, and preferably is 100 μm. Drying air was used at a flow rate of 0.2 to 0.4 m³/min and a temperature of 140 to 160° C. The process conditions and prepared particles' sizes of Examples 26 to 28 are noted in Table 5. The particle size was measured by using dry laser diffraction particle size analysis. In order to check the particles prepared according to the present invention, particles obtained from Example 26 were observed by using a scanning electron microscope. The results are shown in FIG. 8.

Examples 29 to 32

Preparation of Dutasteride Composition Ultra-Fine Particles

Figure 9:
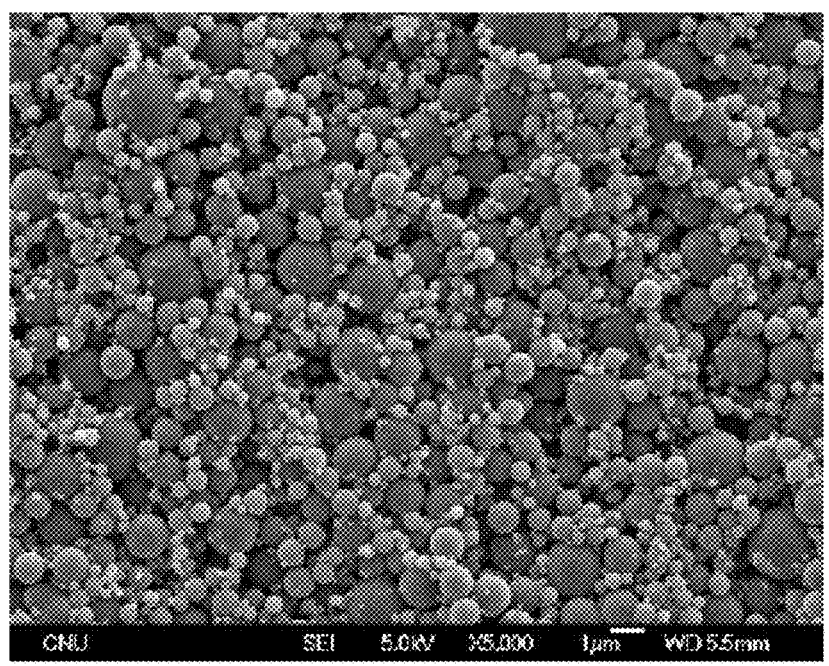

Dutasteride solid dispersion ultra-fine particles were prepared by using a particle preparation process according to the present invention. First, dutasteride, polyvinylpyrrolidone K30, and surfactant were dissolved in ethanol. Previously compressed/heated carbon dioxide and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. The injection amounts of carbon dioxide and chemical solution preferably range from 1 to 50 g/min and from 1 to 30 g/min, respectively. Moreover, the ratio of carbon dioxide and the chemical solution is preferably 1-3. Examples 29 to 32 were carried out at 45° C., and 82 bar, with carbon dioxide and chemical solution in amounts of 40 g/min and 15 g/min. Also, the inside hole size of the coaxial nozzle ranges from 1 to 500 μm, and preferably is 100 μm. Drying air was used at a flow rate of 0.2 to 0.4 m³/min and a temperature of 120 to 150° C. The process conditions and prepared particles' sizes of Examples 29 to 32 are noted in Table 6. The particle size was measured by using dynamic light scattering and laser diffraction particle size analysis. In order to check the particles prepared according to the present invention, particles obtained from Example 32 were observed by using a scanning electron microscope. The results are shown in FIG. 9.

TABLE 5

| Exp | Injection rate of compressed fluid | Injection rate of chemical solution | Solution concentration | Pressure and temp. of heated/compressed gas | Average particle size (dynamic light scattering) | Laser diffraction particle size analysis (on volume) | | | |
|---|---|---|---|---|---|---|---|---|---|
| | | | | | | D10% | D50% | D90% | SPAN |
| 26 | $CO_2$- 40 g/min | 15 g/min | 5 mg/Ml | 200 KPa, 40° C. | 672.4 nm | 0.45 μm | 0.89 μm | 1.65 μm | 1.3 |
| 27 | $CO_2$- 40 g/min | 15 g/min | 10 mg/Ml | 200 KPa, 40° C. | 713.5 nm | 0.49 μm | 0.94 μm | 1.89 μm | 1.5 |
| 28 | $CO_2$- 40 g/min | 15 g/min | 20 mg/Ml | 200 KPa, 40° C. | 767.7 nm | 0.52 μm | 0.99 μm | 2.12 μm | 1.6 |

As shown in Table 5 and FIG. 8, it can be seen that the lysozyme particles prepared according to Examples 26 to 28 are spherical uniform particles with an average particle size of 672.4 to 767.7 nm.

TABLE 6

| Exp | Injection rate of compressed fluid | Injection rate of chemical solution | Pressure and temp. of heated/ compressed gas | composition | Average particle size (dynamic light scattering) | Laser diffraction particle size analysis (on volume base) | | | |
|---|---|---|---|---|---|---|---|---|---|
| | | | | | | D10% | D50% | D90% | SPAN |
| 29 | $CO_2$-40 g/min | 15 g/min | 200 KPa, 80° C. | Chemical solution:PVP 30 = 1:19 | 560.7 nm | 0.45 μm | 0.82 μm | 2.13 μm | 2.0 |
| 30 | $CO_2$-40 g/min | 15 g/min | 400 KPa, 80° C. | Chemical solution:PVP K30:sodium laurylsulfate = 1:15:4 | 505.3 nm | 0.42 μm | 0.88 μm | 1.92 μm | 1.7 |
| 31 | $CO_2$-40 g/min | 15 g/min | 400 KPa, 40° C. | Chemical solution:PVP K30:vitamin ETPGS = 1:15:4 | 850.7 nm | 0.51 μm | 1.43 μm | 2.61 μm | 1.5 |
| 32 | $CO_2$-40 g/min | 15 g/min | 200 KPa, 40° C. | Chemical solution:PVP K30:sucrose ester15 = 1:15:4 | 601.5 nm | 0.49 μm | 1.02 μm | 2.15 μm | 1.6 |

As shown in Table 6 and FIG. 9, it can be seen that the dutasteride solid dispersion prepared according to Examples 29 to 32 include spherical uniform particles, in which 90% or more the particles have a size of less than 3 μm. Also, from differential scanning calorimetry and powder x-ray diffraction analysis, it was determined that dutasteride exists in amorphous forms in solid dispersion.

Examples 33 to 35

Preparation of Itraconazole Composition Ultra-Fine Particles

Itraconazole solid dispersion ultra-fine particles were prepared by using a particle preparation process according to the present invention. First, itraconazole, polyvinylpyrrolidone K30, and surfactant were dissolved in a mixed solution of ethanol and methylene chloride. Previously compressed/heated carbon dioxide and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. The injection amounts of carbon dioxide and chemical solution preferably range from 1 to 50 g/min and from 1 to 30 g/min, respectively. Moreover, the ratio of carbon dioxide and the chemical solution is preferably 1-3. Examples 33 to 35 were carried out at 45° C., and 82 bar, with carbon dioxide and chemical solution in amounts of 40 g/min and 15 g/min. Also, the inside hole size of the coaxial nozzle ranges from 1 to 500 μm, and preferably is 100 μm. Drying air was used at a flow rate of 0.2 to 0.4 $m^3$/min and a temperature of 120 to 150° C. The process conditions and prepared particles' sizes of Examples 33 to 35 are noted in Table 7. The particle size was measured by using dynamic light scattering and laser diffraction particle size analysis.

TABLE 7

| Exp | Injection rate of compressed fluid | Injection rate of chemical solution | Pressure and temp. of heated/ compressed gas | composition | Average particle size (dynamic light scattering) | Laser diffraction particle size analysis (on volume base) | | | |
|---|---|---|---|---|---|---|---|---|---|
| | | | | | | D10% | D50% | D90% | SPAN |
| 33 | $CO_2$-40 g/min | 15 g/min | 300 KPa, 40° C. | Chemical solution:PVP VA64 = 1:5 | 603.5 nm | 0.56 μm | 0.89 μm | 1.82 μm | 1.4 |
| 34 | $CO_2$-40 g/min | 15 g/min | 100 KPa, 40° C. | Chemical solution:PVP VA64:gelucire 44/14 = 1:4:1 | 806.2 nm | 0.53 μm | 1.33 μm | 2.21 μm | 1.3 |
| 35 | $CO_2$-40 g/min | 15 g/min | 50 KPa, 40° C. | Chemical solution:PVP VA64:Vitamin E TPGS = 1:4:1 | 875.2 nm | 0.51 μm | 1.52 μm | 2.89 μm | 1.6 |

As shown in Table 7 and FIG. 9, it can be seen that the itraconazole solid dispersion prepared according to Examples 33 to 35 include uniform particles, in which 90% or more the particles have a size of less than 3 μm. Also, from differential scanning calorimetry and powder x-ray diffraction analysis, it was determined that itraconazole exists in amorphous forms in solid dispersion.

Examples 36 to 40

Preparation of Felodipine Composition Ultra-Fine Particles

Felodipine solid dispersion ultra-fine particles were prepared by using a particle preparation process according to the present invention. First, felodipine, hydroxyl propyl methyl cellulose (HPMC2910), and surfactant were dissolved in a mixed solution of ethanol and methylene chloride. Previously compressed/heated carbon dioxide (or mixture of carbon dioxide and ether, or mixture of carbon dioxide and fluorinated hydrocarbon (R-22, chlorodifluoromethane)) and the prepared solution were injected at a predetermined flow velocity and mixed, and then sprayed through the inside hole of a coaxial nozzle. Meanwhile, through the outside hole of the coaxial nozzle, previously compressed/heated air was sprayed at a predetermined pressure and temperature. Herein, the temperature and pressure range from 30 to 90° C. and from 60 to 300 bar, preferably from 40 to 80° C. and from 75 to 120 bar, respectively. The injection amounts of compressed fluid and chemical solution preferably range from 1 to 50 g/min and from 1 to 30 g/min, respectively. Moreover, the ratio of the compressed fluid and the chemical solution is preferably 1-3. Examples 36 to 40 were carried out at 45° C., and 82 bar, with carbon dioxide and chemical solution in amounts of 40 g/min and 15 g/min. Also, the inside hole size of the coaxial nozzle ranges from 1 to 500 μm, and preferably is 100 μm. Drying air was used at a flow rate of 0.2 to 0.4 m$^3$/min and a temperature of 120 to 150° C. The process conditions and prepared particles' sizes of Examples 36 to 40 are noted in Table 8. The particle size was measured by using dynamic light scattering and laser diffraction particle size analysis.

As shown in Table 8, it can be seen that the felodipine solid dispersion prepared according to Examples 36 to 40 include uniform particles, in which 90% or more the particles have a size of less than 3 μm. Also, from differential scanning calorimetry and powder x-ray diffraction analysis, it was determined that felodipine exists in amorphous forms in solid dispersion.

Test Example 1

Measurement of Average Particle Size and Particle Size Distribution of Prepared Ultra-Fine Particles (D10%, D50%, D90%, SPAN)

The average particle sizes of the ultra-fine particles of various solids obtained from Examples 1 to 39, according to the present invention, were measured by dynamic light scattering. In order to determine the particle size distribution, based on the volume of the particles, D10%, D50%, and D90% were measured by dry laser diffraction particle size analysis. Then, the measured values were used to calculate the following SPAN values.

The SPAN values calculated as above shows particle size distribution of powder, in which a smaller value indicates that the powder has more uniform and dense particle size distribution.

In order to measure the average particle sizes of the prepared ultra-fine particles, each analyte was dispersed in mineral oil to provide a completely dispersed solution. Then, a particle size meter using dynamic light scattering (ELS-8000, Otsuka Electronics, Japan) was used to measure the average particle size. In order to test the particle size distribution of the prepared ultra-fine particles, the analyte was uniformly dispersed in a vacuum of 53 mbar by using air pressure of 1.0 bar, and D10%, D50%, and D90% were measured by a particle size meter using dry laser diffraction particle size analysis (HELOS/RODOS, Sympatec Gmbh, Germany).

Although an exemplary embodiment of the present invention has been described for illustrative purposes, those skilled in the art will appreciate that various modifications, additions and substitutions are possible, without departing from the scope and spirit of the invention as disclosed in the accompanying claims.

TABLE 8

| Exp | Injection rate of compressed fluid | Injection rate of chemical solution | Pressure and temp. of heated/ compressed gas | composition | Average particle size (dynamic light scattering) | Laser diffraction particle size analysis (on volume base) | | | |
|---|---|---|---|---|---|---|---|---|---|
| | | | | | | D10% | D50% | D90% | SPAN |
| 36 | CO$_2$-40 g/min | 15 g/min | 300 KPa, 40° C. | Chemical solution:HPMC = 1:5 | 672.5 nm | 0.51 μm | 0.91 μm | 1.96 μm | 1.6 |
| 37 | CO$_2$-40 g/min | 15 g/min | 100 KPa, 40° C. | Chemical solution:HPMC:poloxamer = 1:4:1 | 820.7 nm | 0.59 μm | 1.46 μm | 2.85 μm | 1.5 |
| 38 | CO$_2$-40 g/min | 15 g/min | 50 KPa, 40° C. | Chemical solution:HPMC:Myrj 52 = 1:4:1 | 1015.2 nm | 0.68 μm | 1.55 μm | 4.1 μm | 2.2 |
| 39 | CO$_2$-35 g/min R-22-5 g/min | 15 g/min | 300 KPa, 80° C. | Chemical solution:HPMC = 1:5 | 667.4 nm | 0.49 μm | 0.90 μm | 1.93 μm | 1.7 |
| 40 | CO$_2$-30 g/min R-22-10 g/min | 15 g/min | 300 KPa, 120° C. | Chemical solution:HPMC = 1:5 | 659.5 nm | 0.48 μm | 0.87 μm | 1.91 μm | 1.6 |

What is claimed is:

1. A method for preparing ultra-fine particles comprising the steps of:
   (a) continuously contacting a liquid solution containing a solute in a liquid solvent with compressed fluid at temperature of 30 to 90° C., and pressure of 60 to 300 bar,
   (b) injecting a resultant product into a mixing unit,
   (c) homogeneously mixing the product to prepare a single-phase mixture;
   (d) spray-drying the mixture together with heated compressed air having a pressure ranging from 50 to 1000 kPa and a temperature ranging from 30 to 120° C. via a nozzle into an atmospheric pressure evaporation chamber in which drying gas flows, to form the ultra-fine particles; and
   (e) collecting the formed ultra-fine particles,
   wherein the nozzle is a device capable of spraying the single-phase mixture comprising the compressed fluid and the liquid solution, together with the heated compressed air, at a spray outflow part, which allows the mixture to contact with the heated compressed air and comprises a multiple-fluid nozzle for two or more fluids, such as a multiple-fluid coaxial nozzle, and
   wherein the ultra-fine particles have a uniform particle size distribution of an average particle size particle size of 0.02~3 micron, in which 10 volume % or less of prepared powder has a size of less than 0.02 micron while 90 volume % or more of the prepared powder has a size of less than 3 micron.

2. The method as claimed in claim 1, wherein the liquid solvent is at least one selected from the group consisting of methanol, ethanol, propanol, isopropanol, butanol, octanol, acetone, methylethylketone, methylisobutylketone, N-hexane, ethylacetate, dichloromethane, chloroform, acetic acid, N-methylpyrrolidone, dimethyl sulfoxide, dimethylamide, and dimethylformamide.

3. The method as claimed in claim 1, wherein the compressed fluid is at least one selected from the group consisting of chlorofluorocarbons, hydrochlorofluorocarbons, hydrofluorocarbons, and fluorocarbons, dimethylether, diethylether, diisopropylether, di-tert-butylether, carbon dioxide and ammonia, and wherein the compressed fluid has a temperature range of 30 to 90° C. and a pressure range of 60 to 300 bar.

4. The method as claimed in claim 1, wherein the mixing unit is a pressure vessel made from metal, ceramic, reinforced glass, copper, which is filled with filler or is mounted with a stirrer, and is for efficiently mixing the liquid solution and the compressed fluid through a maximized contact area between the liquid solution and the compressed fluid.

5. The method as claimed in claim 1, wherein the single-phase mixture has conditions, such as a pressure of 60-300 bar and a temperature of 20-100° C.

6. The method as claimed in claim 1, wherein the drying gas is at least one gas selected from the group including air, nitrogen, and argon, and continuously flows at a temperature of 20 to 300° C. and at a flow rate of 0.1 to 10.0 m$^3$/min.

7. The method as claimed in claim 1, wherein the step (e) is carried out by a metal or polymer filter or net, or a dust-collecting cyclone using air stream.

8. The method as claimed in claim 1, wherein a physiological active substance as a solvate is at least one selected from the group consisting of protein, peptide, nucleotide, functional food, pharmaceutical substances and pharmaceutical preparations.

9. The method as claimed in claim 8, wherein the physiological active substance is at least one selected from the group consisting of cyclosporine, cilostazol, megestrol acetate, lysozyme, dutasteride, itraconazole and felodipine.

10. The method as claimed in claim 8, wherein the physiological active substance used as the solvate comprises a pharmaceutically acceptable additive.

11. The method as claimed in claim 10, wherein the pharmaceutically acceptable additive is at least one selected from the group consisting of hydroperoxy methylcellulose, hydroxypropyl cellulose, polyvinyl pyrrolidone, polyethylene glycol, sodium lauryl sulphate, dioctyl sulfosuccinate, gelatin, casein, lecithin, textran, gum acacia, cholesterol, tragacanth, stearic acid, benzalkonium chloride, calcium stearate, glycerol monostearate, cetostearyl alcohol, cetomacrogol emulsified wax, sorbitan ester, polyoxyethylene alkyl ether, polyoxyethylene castor oil derivative, polyoxyethylene sorbitan fatty acid ester, polyethylene glycol, polyoxyethylene stearate, colloidal silicon dioxide, phosphate, carboxymethylcellulose, calcium, carboxymethylcellulose sodium, methylcellulose, hydroxyethylcellulose, hypromellose phthalate, amorphous cellulose, magnesium aluminium silicate, triethanolamine, polyvinyl alcohol, 4-(1,1,3,3-tetramethylbutyl)-phenolic polymer having ethylene oxide and formaldehyde, poloxamer, block copolymer of ethylene oxide and propylene oxide, poloxamine, tetrafunctional block copolymer derived by sequentially adding propylene oxide and ethylene oxide to ethylenediamine, ethoxylated and propoxylated ethylene diamine, alkyl aryl polyether sulfonate, a mixture of sucrose stearate and sucrose distearate, p-isononylphenoxy-poly(glycidol), a mixture of sucrose cocoate and alcohol, and $C_{18}H_{37}CH_2(CON(CH_3)$—$CH_2(CHOH)_4(CH_2OH)_2$, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-thioglucoside, nonanoyl-N-methylglucamide, n-noyl-β-D-glucopyranoside, octanoyl-N-methylglucamide, n-octyl-β-D-glucopyranoside, octyl-β-D-thioglucopyranoside, PEG-phospholipid, PEG-cholesterol, PEG-cholesterol derivative, PEG-vitamin A, PEG-vitamin E, PEG derived vitamin E, lysozyme, vinylpyrrolidone, and copolymer of vinylacetate.

* * * * *